(12) United States Patent
Challa

(10) Patent No.: US 9,211,521 B2
(45) Date of Patent: Dec. 15, 2015

(54) FLUIDIC CHANNEL COATED WITH METAL CATALYSTS AND DEVICES AND METHODS RELATING THERETO

(71) Applicant: Siva Sai Ramana Kumar Challa, Baton Rouge, LA (US)

(72) Inventor: Siva Sai Ramana Kumar Challa, Baton Rouge, LA (US)

(73) Assignee: MILLIFLUIDICA, LLC, Baton Rouge, LA (US)

( * ) Notice: Subject to any disclaimer, the term of this patent is extended or adjusted under 35 U.S.C. 154(b) by 0 days.

(21) Appl. No.: 14/031,795

(22) Filed: Sep. 19, 2013

(65) Prior Publication Data

US 2014/0094626 A1 Apr. 3, 2014

Related U.S. Application Data

(60) Provisional application No. 61/703,085, filed on Sep. 19, 2012.

(51) Int. Cl.
*B01J 19/24* (2006.01)
*B01J 19/00* (2006.01)
(Continued)

(52) U.S. Cl.
CPC .............. *B01J 19/0093* (2013.01); *B01J 19/24* (2013.01); *B01J 37/0215* (2013.01); *B01L 3/5027* (2013.01); *B01L 3/502707* (2013.01); *B22F 9/18* (2013.01); *B22F 9/24* (2013.01); *C07C 213/02* (2013.01); *B01J 23/42* (2013.01); *B01J 23/44* (2013.01); *B01J 23/464* (2013.01); *B01J 23/50* (2013.01); *B01J 23/72* (2013.01); *B01J 23/745* (2013.01); *B01J 35/006* (2013.01); *B01J 35/0013* (2013.01); *B01J 37/16* (2013.01);

(Continued)

(58) Field of Classification Search
None
See application file for complete search history.

(56) References Cited

U.S. PATENT DOCUMENTS 6,828,143 B1 * 12/2004 Bard ................................ 506/15
8,257,662 B2 * 9/2012 Jin et al. ........................ 422/222
(Continued)

FOREIGN PATENT DOCUMENTS

EP 2492682 B1 2/2012

OTHER PUBLICATIONS

Fan et al. Effect of sodium borohydride on growth process of controlled flower-like nanostructured Cu2O/CuO films and their hydrophobic property. Chemical Engineering Journal 167 (2011) 388-396.*

(Continued)

*Primary Examiner* — Jennifer A Leung
(74) *Attorney, Agent, or Firm* — Billion & Armitage; Sten O. Schuler

(57) ABSTRACT

The invention provides a method for coating fluidic channels, particularly millifluidic channels, with a catalyst coating having controlled dimensions and morphology, and methods for preparing such channels, and devices that can be used in combination with the channels. The invention further provides portable, hand-held millifluidic devices applicable for a wide variety of uses including molecular reduction reactions, in situ material characterization, in situ reaction catalysis characterization, in situ reaction mechanism characterization, nanomaterial synthesis, nanostructured metal and metal oxide growth and coating of channels, continuous flow cell culturing, enzymatic catalysis, biomolecular catalysis, combinatorial chemistry, reactions involving homogeneous catalysts bound to channel walls, peptide synthesis, nucleic acid synthesis, synthesis of pharmaceutical intermediates, biofunctionalization of nanomaterials or a combination thereof.

16 Claims, 9 Drawing Sheets

(51) Int. Cl.
    *C07C 213/02* (2006.01)
    *B22F 9/18* (2006.01)
    *B01J 37/02* (2006.01)
    *B01L 3/00* (2006.01)
    *B22F 9/24* (2006.01)
    *B22F 1/00* (2006.01)
    *B01J 37/16* (2006.01)
    *B01J 37/18* (2006.01)
    *B01J 23/42* (2006.01)
    *B01J 23/44* (2006.01)
    *B01J 23/46* (2006.01)
    *B01J 23/50* (2006.01)
    *B01J 23/72* (2006.01)
    *B01J 23/745* (2006.01)
    *B01J 35/00* (2006.01)
    *B82Y 30/00* (2011.01)
    *B82Y 40/00* (2011.01)

(52) U.S. Cl.
    CPC .......... *B01J 37/18* (2013.01); *B01J 2219/0086* (2013.01); *B01J 2219/00792* (2013.01); *B01J 2219/00835* (2013.01); *B01J 2219/00858* (2013.01); *B01J 2219/00862* (2013.01); *B01J 2219/248* (2013.01); *B01J 2219/2479* (2013.01); *B01L 2300/0816* (2013.01); *B01L 2300/0867* (2013.01); *B01L 2300/0883* (2013.01); *B01L 2300/16* (2013.01); *B01L 2300/161* (2013.01); *B01L 2400/0487* (2013.01); *B22F 1/0018* (2013.01); *B22F 2001/0037* (2013.01); *B82Y 30/00* (2013.01); *B82Y 40/00* (2013.01)

(56) References Cited

U.S. PATENT DOCUMENTS

| | | | |
|---|---|---|---|
| 2003/0012697 A1* | 1/2003 | Hahn et al. | 422/99 |
| 2003/0054558 A1* | 3/2003 | Kurabayashi et al. | 436/63 |
| 2004/0031592 A1 | 2/2004 | Mathias et al. | |
| 2006/0150385 A1* | 7/2006 | Gilligan et al. | 29/407.08 |
| 2008/0214884 A1* | 9/2008 | Daly et al. | 585/700 |
| 2009/0215158 A1* | 8/2009 | Sekizawa et al. | 435/287.2 |
| 2010/0303687 A1 | 12/2010 | Blaga et al. | |
| 2011/0112348 A1 | 5/2011 | Tonkovich et al. | |
| 2011/0123413 A1 | 5/2011 | Abate et al. | |
| 2011/0126910 A1 | 6/2011 | May | |
| 2013/0206250 A1 | 8/2013 | Zhang et al. | |

OTHER PUBLICATIONS

Rebrov et al. Capillary microreactors wall-coated with mesoporous titania thin film catalyst supports. Lap on a Chip, vol. 9, No. 4, Feb. 21, 2009, 503-506.*

Abahmane et al., "Synthesis of polypyridine derivatives using alumina supported gold nanoparticles under micro continuous flow conditions," Chemical Engineering Journal (2011) 167: 519-526.

Biswas et al., "Developing a Millifluidic Platform for the Synthesis of Ultrasmall Nanoclusters: Ultrasmall Copper Nanoclusters as a Case Study," Small (2012) 8 (5): 688-698.

Li et al., "Size Evolution of Gold Nanoparticles in a Millifluidic Reactor," ChemPhysChem (2011) 1-7.

Lorber et al., "Some recent advances in the design and the use of miniaturized droplet-based continuous process: Applications in chemistry and high-pressure microflows," Lab Chip (2011) 11: 779-787.

* cited by examiner

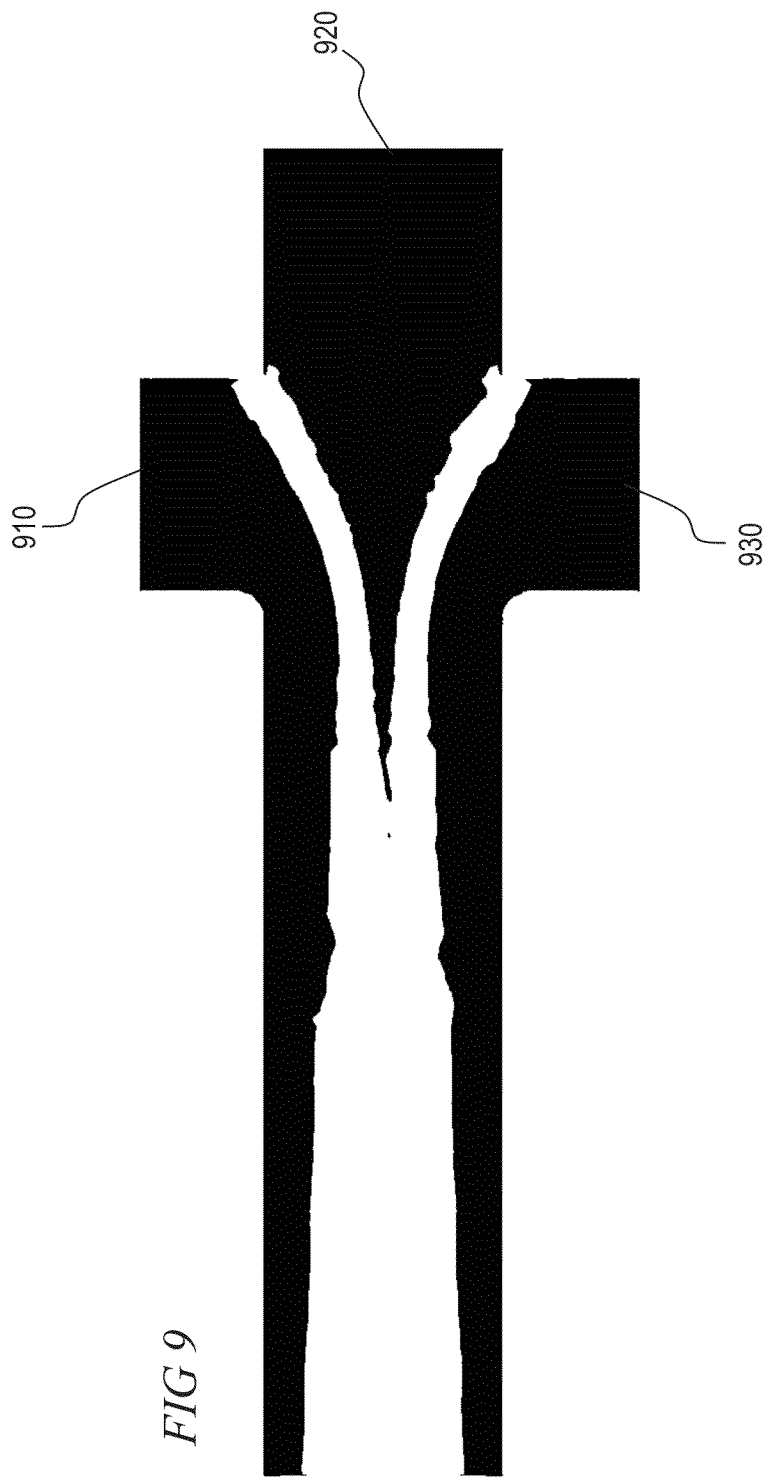

FLUIDIC CHANNEL COATED WITH METAL CATALYSTS AND DEVICES AND METHODS RELATING THERETO

RELATED APPLICATIONS

This application claims priority under 35 U.S.C. §119(e) to U.S. Provisional Patent Application No. 61/703,085, filed Sep. 19, 2012, which is incorporated herein by reference.

BACKGROUND OF THE INVENTION

A number of synchrotron radiation-based X-ray characterization tools are used for both chemical and physical characterization of materials, especially in a liquid environment. Among these, X-ray absorption spectroscopy (XAS) is a versatile tool to probe oxidation states, coordination, and local order of materials, even in the absence of a crystalline lattice. XAS has been used to investigate the electronic and geometric structures of nanomaterials; more specifically, to map local coordination number, the extent of alloying and composition of multi-metallic systems in solution. Further, in situ XAS offers an opportunity to observe time-resolved bond formation, changes in oxidation states, coordination, and local order. The ability to follow the fundamental processes in the synthesis of nano structured materials with atomic precision is an unfulfilled need in the field of nanoscience.

Microfluidic systems have been used to prepare a wide range of materials. These systems consist of small channels of micrometer dimensions in which the reactive liquid precursors needed to produce solid clusters of metals are mixed and allowed to react. Recently, they have become an attractive technology due to their ability to rapidly mix reagents, provide homogeneous reaction environments, continuously vary reaction conditions, add reagents at precise time intervals during reaction, and the ability to control the residence time by varying the reactant flow-rates and/or the length of the flow channel. These features have been cleverly utilized in the wet-chemical synthesis of nanomaterials not only to control their size, size-distribution, and shape, but also to control their crystal structure and for faster clinical translation.

The use of XAS in conjunction with microfluidic systems provides a powerful new method for in situ time-resolved experiments probing the structure and reaction dynamics at atomic level. However, a major drawback of microfluidic chips is the inability to obtain high quality data from techniques such as in situ XAS for sample concentration in excess of 0.1 M. Thus, new techniques and devices are needed to overcome these drawbacks.

Additionally, there are problems in coating fluidic channels with catalysts having controlled dimensions and morphology. A catalyst coating having controlled dimensions and morphology is important for carrying out chemical reactions and characterization of the same while also preventing channel clogging. Controlled morphology of the catalyst is required for better catalysis and also for continuous flow synthesis. Accordingly, there is a need for methods for coating fluidic channels with catalysts having controlled dimensions and morphology, particularly where the coating avoids or prevents channel clogging.

Further, there is a need for hand-held and user friendly devices for coating channels with catalyst and other structures having controlled dimensions and morphology, and for carrying out processes such as chemical and biological reactions, characterization, continuous flow cell culturing, enzymatic catalysis, biomolecular catalysis, reactions involving homogeneous catalysts bound to channel walls, peptide synthesis, nucleic acid synthesis, synthesis of pharmaceutical intermediates, biofunctionalization of nanomaterials, combinatorial chemistry, and others.

SUMMARY

The invention provides devices having catalyst coatings within fluidic channels in a controlled manner. The control is seen in at least three significant ways. First, the coating dimensions can be controlled. This includes both the size of catalytic nanostructures, and the area over which they are grown throughout the millifluidic channels. Second, the growth location of the catalytic coating can be controlled. For example, FIG. 1A-C show a thin strip of gold catalyst coating within the center of channels having a width of approximately 200 microns. Catalytic coatings can also be grown throughout the entire channel by varying conditions such as flow rate, precursor injection location, and other variables which affect the flow system's Reynolds number. Third, the morphology of the catalyst coating can be controlled with micro and nanoscopic precision. Petalled flower-like structures, half-hemisphere structures, porous surfaces, and permutations thereof are among the achievable morphologies which enhance catalytic activity, as can be seen in FIG. 2. The reactants, which react catalytically with the catalyst, can flow through the channels and the product is obtained at the outlet without any clogging due to the millifluidic scale of the channels and the size of nanostructures grown within. The invention thus provides a method for coating fluidic channels with catalysts having controlled dimensions and morphology.

The invention further provides hand-held millifluidic devices which may be used for molecular reduction reactions, in situ material characterization, in situ reaction catalysis characterization, in situ reaction mechanism characterization, nanomaterial synthesis, nanostructured metal and metal oxide growth and coating of channels, enzyme catalyzed reactions, bio-reactions, combinatorial chemistry, reactions involving homogeneous catalysts bound to channel walls, peptide synthesis, nucleic acid synthesis, synthesis of pharmaceutical intermediates, biofunctionalization of nanomaterials and continuous flow cell culturing.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 1A'. Illustration and spectroscopic data of a thin layer of gold catalyst coating within the center of the channels, particularly a width profile within the millifluidic channels within the millifluidic channels after 1 h flow-time and relating to FIG. 1A and FIG. 1A", according to some techniques of the disclosure.

FIG. 1A''. Illustration and spectroscopic data of a thin layer of gold catalyst coating within the center of the channels, particularly a thickness profile within the millifluidic channels after 1 h flow-time and relating to FIG. 1A and FIG. 1A', according to some techniques of the disclosure.

FIG. 1B'. Illustration and spectroscopic data of a thin layer of gold catalyst coating within the center of the channels, particularly a width profile within the millifluidic channels within the millifluidic channels after 5 h flow-time and relating to FIG. 1B and FIG. 1B'', according to some techniques of the disclosure.

FIG. 1B''. Illustration and spectroscopic data of a thin layer of gold catalyst coating within the center of the channels, particularly a thickness profile within the millifluidic channels after 5 h flow-time and relating to FIG. 1B and FIG. 1B', according to some techniques of the disclosure.

FIG. 1C'. Illustration and spectroscopic data of a thin layer of gold catalyst coating within the center of the channels, particularly a width profile within the millifluidic channels within the millifluidic channels after 9 h flow-time and relating to FIG. 1C and FIG. 1C'', according to some techniques of the disclosure.

FIG. 1C''. Illustration and spectroscopic data of a thin layer of gold catalyst coating within the center of the channels, particularly a thickness profile within the millifluidic channels after 9 h flow-time and relating to FIG. 1C and FIG. 1C', according to some techniques of the disclosure.

FIG. 9: A top view of a hydrodynamically focused flow channel.

DETAILED DESCRIPTION

Figure 1A:
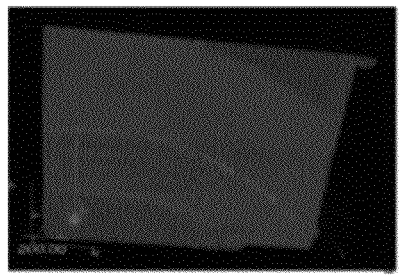
FIG. 1A. Illustration and spectroscopic data of a thin layer of gold catalyst coating within the center of the channels, particularly a 3-D X-ray tomographic image of gold formed (marked by arrows) within the millifluidic channels after 1 h flow-time and relating to FIG. 1A' and FIG. 1A", according to some techniques of the disclosure.
Figure 1A:
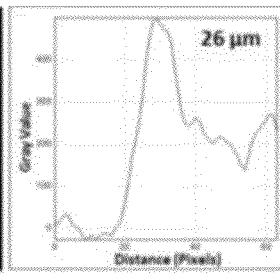
Figure 1A:
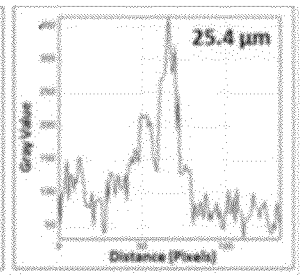

Currently, there is a problem in coating fluidic channels with catalysts having controlled dimensions and morphology. Controlled dimension of the coating is important to prevent clogging. Controlled morphology of the catalyst is also needed for improved catalyst efficacy, particularly in continuous flow catalysis. The invention described herein solves these two problems.

The technology described herein differs significantly from what currently exists in the field. Currently, there is no process or method available prior to this disclosure to coat fluidic channels with catalysts having controlled dimensions and morphology (see De Jong, Krijn P. (ed.), *Synthesis of Solid Catalysts*, May 2009, Wiley-VCH, Weinheim). Currently used approaches have several drawbacks as follows.

In one approach, a catalyst is typically supported on a catalyst support and tested in a reaction flask. The disadvantages of this approach is that there is a need for preparing the supported catalyst and it needs to be separated and reused after the reaction (see Gaur, Miller, Stellwagen, Sanampudi, Kumar, and Spivey, *Synthesis, characterization, and testing of supported Au catalysts prepared from atomically-tailored Au38(SC12H25)24 clusters, Phys. Chem. Chem. Phys*, 2012, 14(5), 1627-1634; and Turner et al., *Nature*, 454, 981-983, 2008). Another disadvantage is the poor reproducibility and process control of the supported catalyst preparation.

In a second approach, catalysts are supported within large columns and the reagents are flown through such fixed bed reactor columns (see De Jong, Krijn P. (ed.), *Synthesis of Solid Catalysts*, May 2009, Wiley-VCH, Weinheim). The disadvantage with this approach is that there is no control over the structure of the catalyst (the micro and nano precision) and hence the surface area of the catalysts.

In a third approach, the catalysts are embedded within microfluidic channels and catalysis is carried out as in the previous case [Ismagilov et al., *Oxidation of organic compounds in a microstructured catalytic reactor, Chemical Engineering Journal*, 2008, 135S, S57-S65). However, fabrication of microfluidic catalyst beds is expensive and impractical for large numbers of experiments.

Chip-based millifluidics, and related hand-held apparatus, as disclosed herein, offer a technology very different from tubular millifluidics with demonstrated advantages over traditional microfluidics for higher throughput controlled synthesis of ultrasmall nanoclusters and as probes for mapping time-resolved growth of nanomaterials. A central theme of these novel investigations is the utility of millifluidics for mapping the time-resolved chemistry of the growth of metallic structures in general and catalysts in particular.

Also provided is a demonstration of continuous flow catalytic activity of the as-formed gold nanostructures, for example, the reduction of 4-nitrophenol and ferricyanide. While microfluidics-based continuous flow catalysis of gold nanoparticles impregnated on alumina has been previously utilized for synthesis of polypyridine derivatives, the ability to control the dimension, and morphology of the embedded gold nanostructured catalysts within continuous flow channels can provide superior continuous flow catalysis applications. With the ability to embed atomically precise catalysts, these tools can revolutionize catalysis from the point of view of practical as well as fundamental investigations. Such systems can also lead to advances in the field of bio-sensing, electrophoresis, and enhanced optical detection. Additionally, the flower-like gold morphology obtained through this formation process has applications in surface-enhanced Raman spectroscopy, catalysis, bio-imaging, and super-hydrophobic coatings.

Definitions

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more channels on a microchip can refer to about 1 to about 100 channels, or about 100 to about 1000 channels.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

A "microfluidics system" refers to a system that has fluidic channels with a tubular diameter in the micrometer dimension. As used herein, the term "micrometer dimension" refers to dimensions in micron size, for example, 0.5 μm to about 100 μm, or about 1 μm to about 90 μm.

A "millifluidics system" refers to a system that has fluidic channels with a tubular diameter in millimeter dimension. As used herein, the term "millimeter dimension" refers to dimensions in millimeter size, for example, about 0.10 mm to about 1000 mm, about 1 mm to about 100 mm, about 1 mm to about 10 mm, about 0.15 mm to about 10 mm, or about 2 mm to about 20 mm.

As used herein, the term "controlled dimension" refers to the ability to control the size, shape, and characteristics of a structure. Particularly, controllable dimensions may include overall diameter, hemispherical shapes, flower-like petalled, shapes, pores, smooth surfaces, and others. "Controlled dimension" may also refer to the ability to control the area of deposition and the width and thickness of the deposition.

As used herein, the term "morphology" refers to "nanostructured" surfaces or features, which means that the coating is in the form of grains having nm dimensions, e.g., 1-100, or about 1-100 nm in diameter grains.

As used herein, the term "catalyst" refers to a material that lowers activation energy of a reaction, enhance reaction speed, yield, quality of reactions products, or selectivity of a particular reaction product. As used herein, "catalyst" will typically refer to metals, metal oxides, and various combinations and permutations of these either different metals or different metal oxides, or a combination of metals and metal oxides, however "catalyst" may refer to other elements, compounds, compositions, or enzymes such as lipases, polymerases, synthases, or catalytic RNA molecules which catalyze biochemical reactions.

As used herein, the term "Renolds Number" refers to a dimensionless quantity that gives a measure of the ratio of inertial forces to viscous forces and consequently quantifies the relative importance of these two types of forces for given flow conditions. The Reynolds number delimiting laminar and turbulent flow depends on the particular flow geometry, and moreover, the transition from laminar flow to turbulence can be sensitive to disturbance levels and imperfections present in a given configuration As used herein, the term "laminar flow" refers to flow through a straight pipe having a substantially circular cross section with a Reynolds number less than about 2040.

As used herein, the term "turbulent Flow" refers to flow through a straight pipe having a substantially circular cross section with a Reynolds number greater than about 2040.

As used herein, the term "precursor" refers to starting materials, and typically will refer to the initial chemicals or compounds introduced into the millifluidic channels. For example $HAuCl_4$ as a precursor for coating channels with metallic gold catalyst.

As used herein, the term "reagent" refers to any chemical used for a reaction or process. A chemical may be a reaction reactant, surfactant, stabilizer, or other chemical compound or element.

As used herein, the phrase "colloidal stability" refers to the stability of a colloidal system and is the capability of the system to remain as it is, without, for example, aggregation and settling in the case of droplets, or layer separation in the case of droplets.

As used herein, the phrase "molecular reduction reactions" refers to chemical reactions leading to reduction of molecules to lower oxidation state. For example, the oxidation state of gold in the precursor salt $HAuCl_4$ is 3 and is reduced to metallic gold with an oxidation state of zero.

As used herein, the phrase "in situ material characterization" refers to characterization of materials during their formation. Characterization may include determining the size, shape, quality, or composition of materials. For example during the formation of gold nanoclusters starting from a gold salt precursor, one can monitor and understand the nucleation process and how nuclei combine together to form a cluster of a specific size.

As used herein, the phrase "in situ reaction catalysis characterization" refers to refers to characterization of a catalytic reaction during catalysis. Characterization may include determining reaction yield and intermediates.

As used herein, the phrase "in situ reaction mechanism characterization" refers to characterization of reaction mechanism while the reaction is going on. Characterization may include determining reaction intermediates. For example, during the formation of intermediate Au-s nanoparticles before formation of metallic Au nanoparticles, the intermediates may not be stable or exist fleetingly. In situ characterization techniques can be used to identify chemical and physical characteristics of these fleeting or unstable intermediates.

As used herein, the "phrase nanomaterial synthesis" refers to the synthesis of materials in nano dimensions, typically within the range of about 1-1000 nm. Nanomaterial synthesis may also refer to the synthesis of materials having characteristics or features which are nano in scale, or have sizes within the range of about 1-1000 nm.

As used herein, the phrase "continuous flow cell culturing" refers to cell culturing in a medium that is flowing continuously. This is different from cell cultures in s stationery medium such as petri dishes.

As used herein, the phrase "combinatorial chemistry" refers to refers to chemical synthetic methods that make it possible, by using a number of chips, to simultaneously to prepare a large number (tens to thousands or even millions) of compounds in a single process. It also means simultaneously carrying a single reaction with different parameters using a number of chips in a single device.

As used herein, the phrase "spatial resolution" refers to the spatial density of the image and optical resolution of the microscope used to capture the image. The number of pixels contained in a digital image and the distance between each pixel (known as the sampling interval) are a function of the accuracy of the digitizing device. The optical resolution is a measure of the microscope's ability to resolve the details present in the original specimen, and is related to the quality of the optics, sensor, and electronics in addition to the spatial density (the number of pixels in the digital image). In situations where the optical resolution of the microscope is superior to the spatial density, then the spatial resolution of the resulting digital image is limited only by the spatial density.

As used herein, the phrase "time resolution" refers to the ability to monitor a given characteristic, quantity, concentration, or the like, at a certain time interval. For example, the products formed within millifluidic channels can be analyzed with a time resolution of 5.4 ms. That is, every 5.4 ms characteristics such as size or shape may be obtained for the products formed within millifluidic channels.

Ultra-small nanoclusters (UNCs), defined to be in the size range 1-2 nm (<100 atoms), form a bridge between atoms and nanoparticles and exhibit molecule-like unique behavior (optical, magnetic, catalytic properties) owing to their quantum size effects, and surface characteristics. While they hold immense potential in a number of fields ranging from sensors, microelectronics, biotechnology, energy and catalysis, their size and morphology-controlled synthesis is key for exploiting their applications, especially for catalysis.[1] Particularly, catalytic structures having sizes or morphological features, such as outgrowths or pores, within the 1-1000 nm range are of interest.

The formation of ultra-small metal nanoclusters according to some methods is generally comprised of the following steps namely nucleation, particle growth, surface capping and/or agglomeration; although there could be overlapping steps. In order to prepare well-defined and size-controlled ultra-small metal nanoclusters, what is required is a fast nucleation rate followed by separation of nucleation and growth phases along with an efficient surfactant to prevent agglomeration and to assist in colloidal stability.

Wet-chemical synthesis using 'lab-on-a-chip' platform is an effective tool for synthesis of nanoparticles as the reactions can be carried out in a steady state with better control over addition of reagents, efficient mixing (when proper mixers are incorporated) and reproducibility compared to the conventional batch or flask processes. Furthermore, continuous flow 'lab-on-a-chip' reactors offer minimal consumption of reagents during optimization process and improved control on temperature and residence time behavior within the reactor volume. In these reactors, because of the possibilities for rapid mixing and efficient heat and mass transfer due to large surface to volume ratio, the nucleation and growth phases can be separated. This has been demonstrated in the case of microfluidic reactors where nanoparticles with defined size, size-distribution and shape have been synthesized by varying not only the design of the reactor but also various reaction parameters and flow rates.

However, what is obvious from these investigations is the need for complicated microfluidic reactor designs, for example, segmented gas/liquid flow reactors, in order to control the particle size and size distribution. In addition, particle characteristics were found to be profoundly influenced by parameters such residence time and residence time distribution (RTD) and velocity profiles.

Millifluidic platform as a novel approach for reproducible, high throughput and controlled synthesis of UNCs. The platform is based on a simple and "inexpensive to fabricate" millifluidic chip model which offers similar control over flow rates and manipulation of reagents as traditional microfluidic reactors which are geometrically constrained to sub-millimeter scales. Through numerical simulations supported by experimental results, high flow rates can be generated within millifluidic space due to, among other things, lower pressure drops and the ability to withstand higher operating pressures. These characteristics lead to dramatic decrease in residence times thereby offering the possibility to generate ultra-small nanoclusters. While it is theoretically possible to obtain similar residence times and throughput in microfluidic systems at the expense of a higher pressure drop, their fabrication is not trivial as it would depend very strongly on the robustness of various bonded surfaces in the device—microchannel-to-substrate or interconnects-to-microchannel. In addition, they offer a more generalized and efficient platform for time-resolved kinetic studies with higher signal to noise ratio than what has been possible so far with microfluidics.

Scaling up of microfluidic chips into millifluidic ones presents some considerable advantages over microfluidics while retaining similar or superior flow characteristics. One is the low cost for fabrication of millifluidic chips which can be accomplished without lithography, which is necessary for fabricating chips on a microfluidic scale. Millifluidic chips are usually produced by using precision micromachining to fabricate metal mold inserts, injection molding for cost-effective chip replication, and lamination for adequate sealing of the devices/chips. Since the connecting capillary tubes and the various modules of the system can be assembled and disassembled easily, the modular setup can be realized on demand in a short time.

Presented herein is a basic concept of millifluidics as an effective platform for controlled and high throughput synthesis of UNCs. In one example embodiment, the concept involves a polymeric millifluidic reactor wherein by varying different flow rates and using a facile aqueous based one step reduction process of the copper (II) salts under inert atmospheric conditions, UNCs are obtained. In some approaches, a novel bidentate water-soluble thiolated polymeric surfactant is utilized, which provides exceptional colloidal stability. Either methods produce UNCs which are catalytically active.

By adjusting the flow rates and concentrations of precursor solutions within a fluidic channel and carrying out the coating process in two different steps, the techniques described herein provide coating of the channels with catalysts having controlled dimensions and morphology.

Millifluidic devices and coating methods described herein provide the ability to coat fluidic channels with catalytic structures having controlled dimensions and morphology, wherein particular morphological features may range from about 1-1000 nm, and overall growth structures may range from about 0.01 to about 5,000 microns in diameter. Catalytic structures may have pores ranging from about 1 to about 500 nm in diameter, from about 1 to about 250 nm in diameter, from about 1 to about 150 nm in diameter, or from about 1 to about 50 nm in diameter. For example, the millifluidic devices and methods as described herein may be used to deposit catalytic structures having sizes of up to about 5,000 microns in diameter, with overall size being controllable with nano-scale precision, and with morphological features being simultaneously controllable with nano-scale precision. Morphology may similarly be controlled by varying process conditions and other factors as will be described herein. These devices and methods deliver highly active catalytic growth sites which obviate the agglomeration and clogging problems inherent to microfluidic devices. Furthermore, there are problems of agglomeration and clogging. The methods can be utilized in producing catalyst test kits or devices consisting of a box containing pumps, chips, and containers, such as those shown in FIG. 3A-D, which may all be further integrated into hand-held and user friendly millifluidic devices.

Figure 4A:
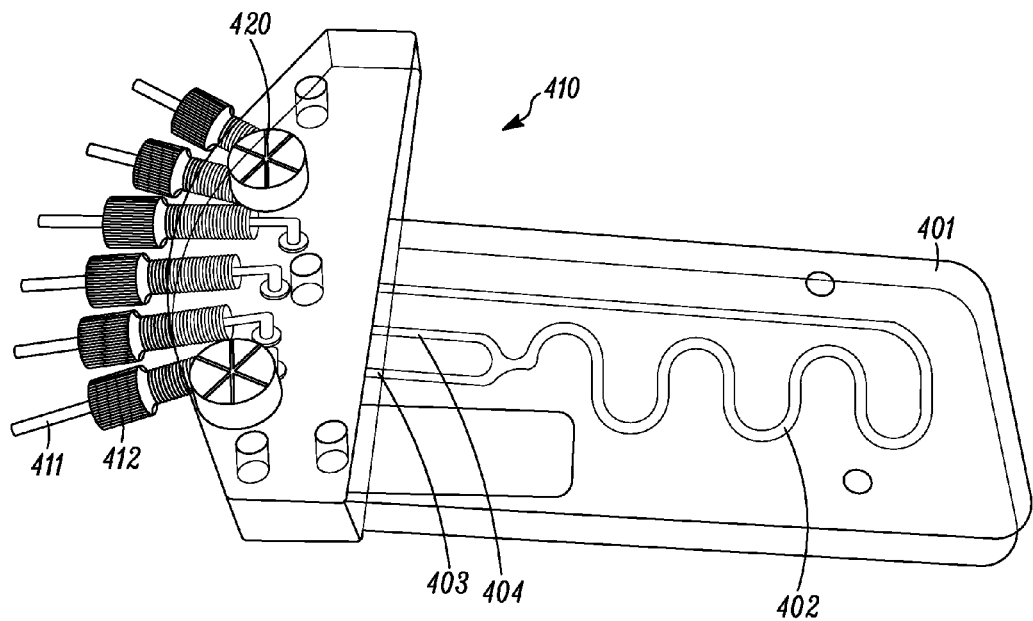
FIG. 4A. A perspective view of a Millifluidic chip coupled to a manifold, both parts were purchased from Millifluidica, LLC (Baton Rouge, La.).
Figure 4B:
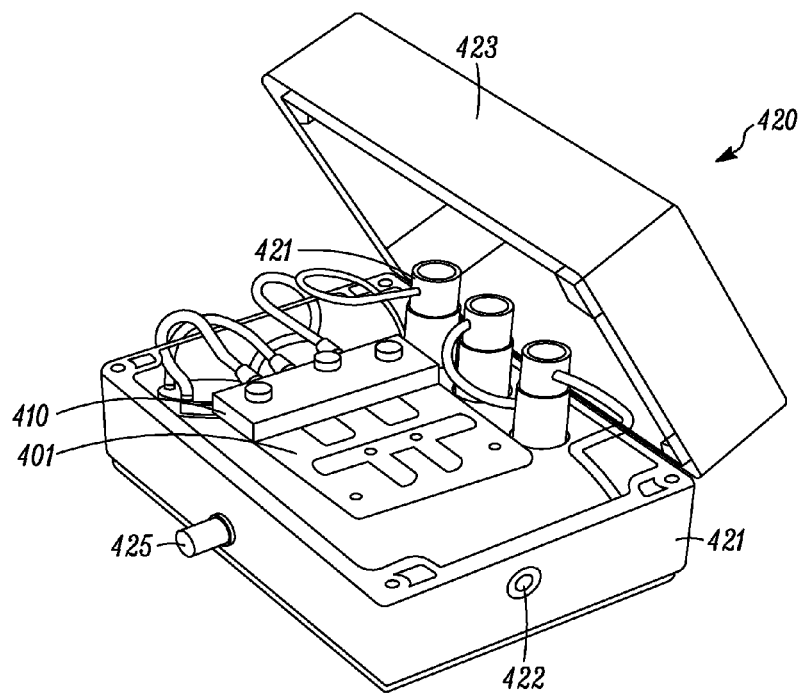
FIG. 4B. A perspective view of a hand-held Millifluidic device purchased from Millifluidica, LLC (Baton Rouge, La.).

FIG. 4A shows a millifluidic chip 401 connected to a manifold 410 and various related components, including a primary channel 402, two supply channels, 403 and 404, multiple reagent lines 411 which connect via an adaptor 412 to the manifold 410. The millifluidic chip 401 may be connected to the manifold 410 by various means, such as the connection knobs 420 shown. FIG. 4B shows an example millifluidic device 420 which incorporates a millifluidic chip 401 and manifold 410 with reagent lines 411 running to product or reactant reservoirs which may contain pumps, flow controllers, and other elements. A flow control interface knob 425 is shown protruding from the device housing 421, in addition to a power connection point 422 which may connect to, for example, a 24 V DC adapter. Such a device may be scaled up to incorporate 10, 100, or 1,000 millifluidic chips. While millifluidic chips have demonstrated advantages over other fluidic chips, such as microfluidic chips, fluidic chips of other scales may be incorporated into such a device. Such millifluidic devices may also comprises a cover 423 which may be clear, tinted, or completely opaque. Non-transparent covers may be preferred where reactants, products, or catalysts are sensitive to light or other external elements.

Various embodiments of the invention include the following Steps.

1. Flowing a precursor metal salt solution at a specific flow rate and for certain specific period of time;
2. Washing the channels to remove the unadhered chemicals;
3. Flowing a reducing agent solution to convert the precursor into metal catalyst; and
4. Washing the channels to remove unreacted chemicals, leaving behind metal catalyst structures having controlled sizes, morphologies, growth region locations, or combinations thereof.

Steps 1 and 3 are important and necessary for obtaining efficient catalyst coating with highly controlled morphology. The flow rate and time period for flow are important in the first step.

Steps 2 and 4 are designed to effectively clean the channels after a reaction is carried out. The steps should be carried in the order of 1, 2, 3, and 4 to maximize the beneficial results. In some embodiments, Steps 1 and 2, and Steps 3 and 4, respectively, may be combined.

Figure 1B:
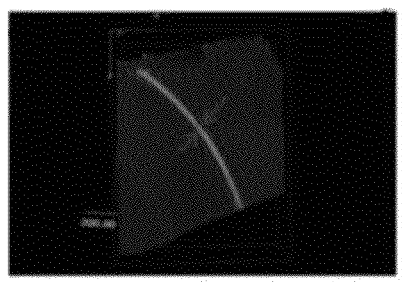
FIG. 1B. Illustration and spectroscopic data of a thin layer of gold catalyst coating within the center of the channels, particularly a 3-D X-ray tomographic image of gold formed (marked by arrows) within the millifluidic channels after 5 h flow-time and relating to FIG. 1B' and FIG. 1B'', according to some techniques of the disclosure.
Figure 1B:
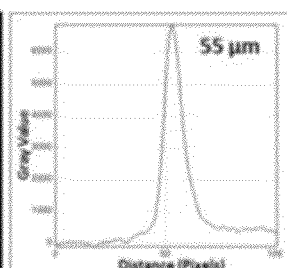
Figure 1B:
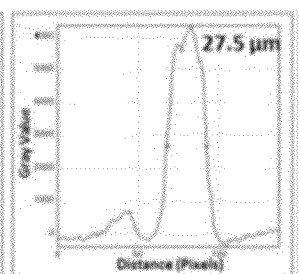
Figure 1C:
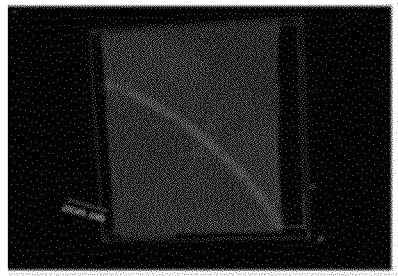
FIG. 1C. Illustration and spectroscopic data of a thin layer of gold catalyst coating within the center of the channels, particularly a 3-D X-ray tomographic image of gold formed (marked by arrows) within the millifluidic channels after 9 h flow-time and relating to FIG. 1C' and FIG. 1C'', according to some techniques of the disclosure.
Figure 1C:
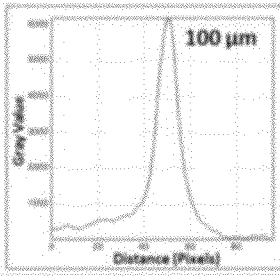
Figure 1C:
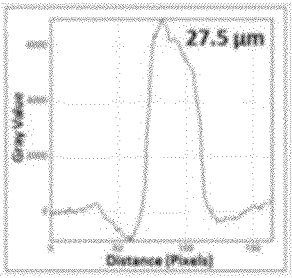
Figure 2:
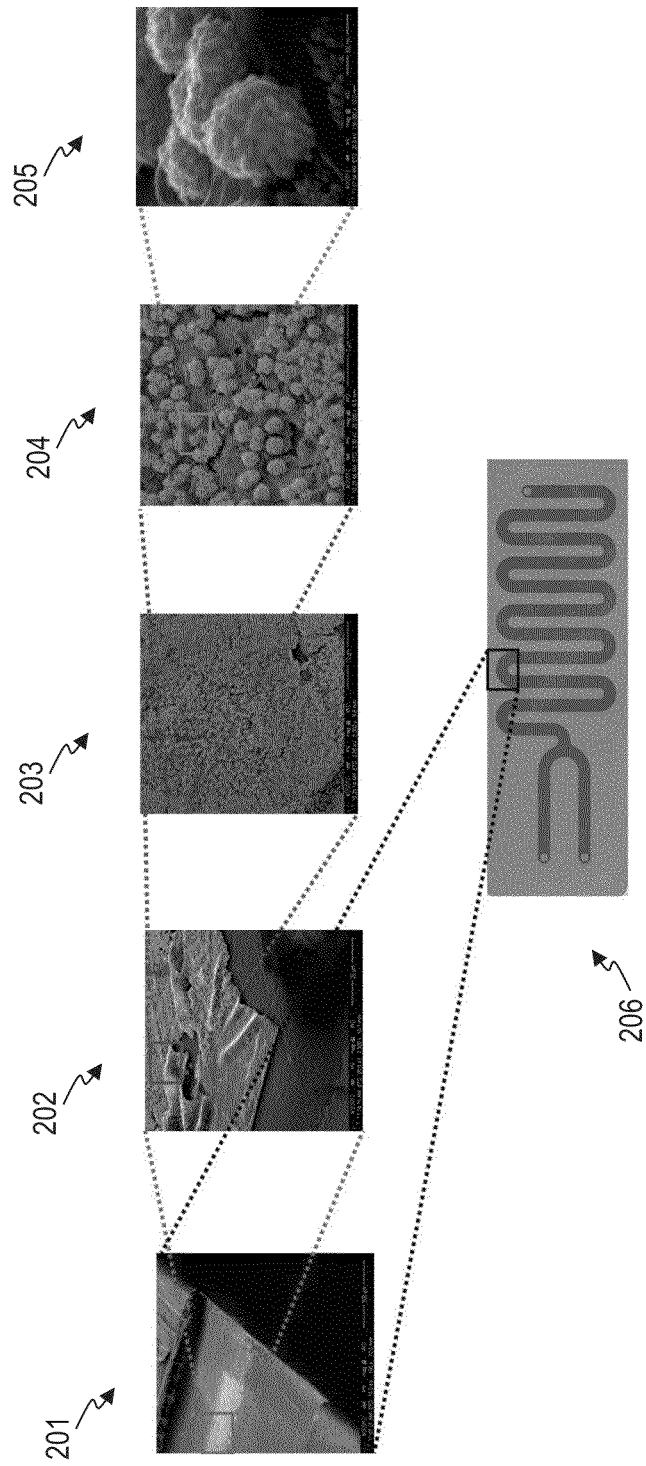
FIG. 2. A millifluidic channel coated with gold catalyst showing micro and nanoscopic control over preparation of the catalyst within the millifluidic channels.
Figure 3B:
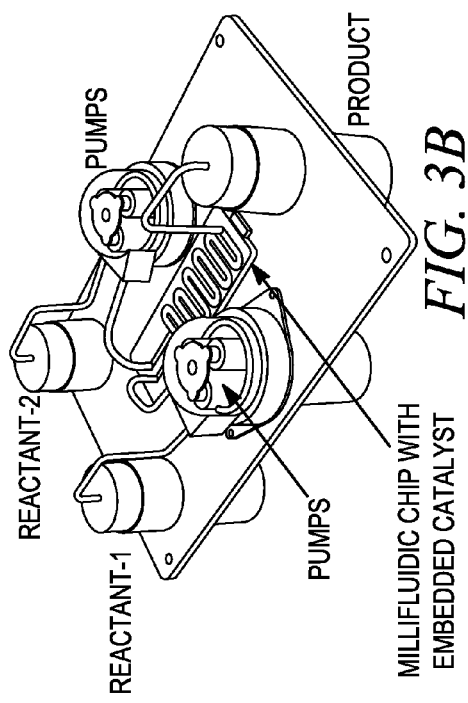
FIG. 3B. A perspective view of a millifluidics device mother board consisting of a millifluidic catalyst test strip connected through tubing to reactant solutions, pumps and product collector.
Figure 3D:
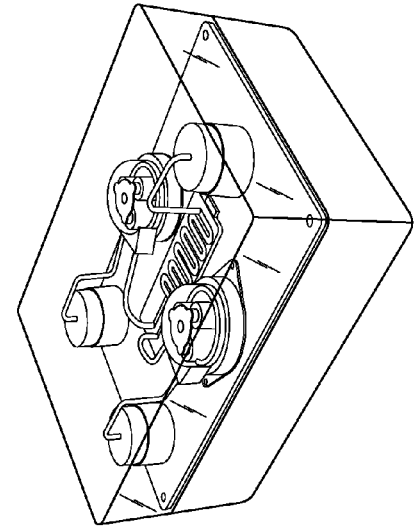
FIG. 3D A perspective view of a millifluidics device mother board packaged within a 17×12×10 cm$^3$ box, shown with the lid closed.
Figure 3A:
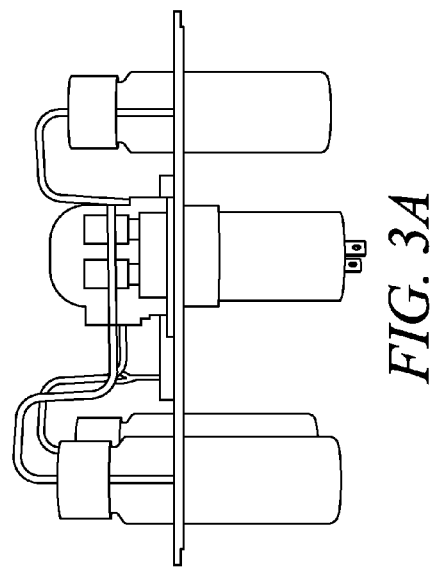
FIG. 3A. A perspective view of a millifluidics device mother board consisting of a millifluidic catalyst test strip connected through tubing to reactant solutions, pumps and product collector.
Figure 3C:
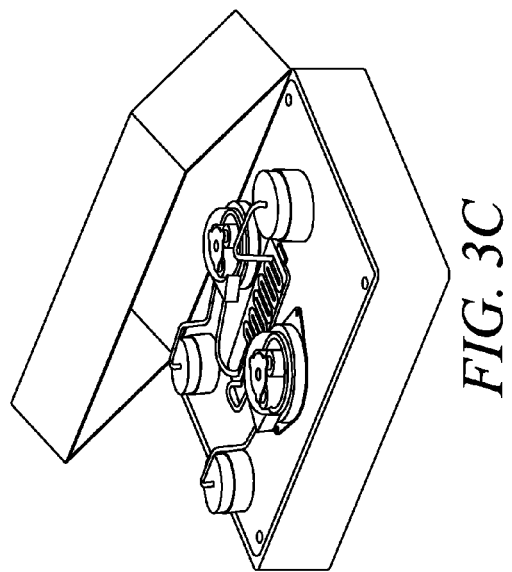
FIG. 3C A perspective view of a millifluidics device mother board packaged within a 17×12×10 cm$^3$ box, shown with the lid open.

The invention works in two separate steps, although the two separate steps can be combined into one. In a first step (1), reagent solutions are flowed through catalyst coated millifluidic channels for a certain period and at a certain specific flow rate. In Step 3, a reducing agent solution is flowed for a certain period at a certain flow rate resulting in a coating of the metal catalyst having controlled dimensions and morphology. A typical experimental procedure to coat gold catalyst having controlled dimensions and morphology, as shown in FIG. 1A-C and FIG. 2, within a millifluidic channel is provided in Example 1, below. FIG. 2 shows catalyst coating inside the millifluidic channel. 201 shows less than 100 micron wide catalysts coating within the channel. 202 shows further magnified image of the coating revealing close-up of the layer of coating. 203 shows nanoparticulate structure on the surface of the catalyst coating. 204 shows nanoparticles further grown into bigger micron size particles. 205 shows the micro size particles with nanoscopic pores. 206 represents the millifluidic chip.

Precursor salts that can be used in coating respective metal catalysts within the millifluidic channels include gold salts, platinum salts, palladium salts, copper salts, silver salts, rhodium salts, and the like. Specific examples of metal salts which may be used are chloroplatinic acid ($H_2PtCl_6$) for platinum coatings; palladium(II) chloride ($PdCl_2$) for palladium coatings; copper(II) chloride ($CuCl_2$) for copper coatings; silver nitrate ($AgNO_3$) for silver coatings, iron(III) chlorides and/or iron(II) chlorides for iron or iron oxide coatings, rhodium chloride for rhodium coatings, cobalt chloride for cobalt coatings, and a combination of these salts for multi-metallic catalyst coatings. These can be core-shell type or alloy type multi-metallic coatings.

Reducing agents that can be used in coating respective metal catalysts within the millifluidic channels include $NaBH_4$, lithium aluminum hydride ($LiAlH_4$), DMSA, diborane, hydrazine, hydrogen, diisobutylaluminum hydride (DIBAL-H), oxalic acid ($C_2H_2O_4$), formic acid ($HCO_2H$), ascorbic acid ($C_6H_8O_6$), or combinations thereof.

Figure 5A:
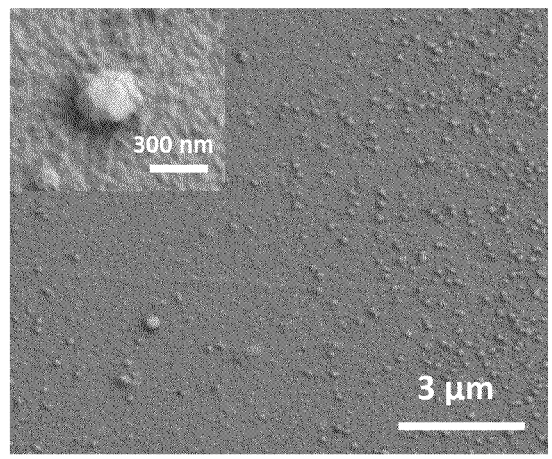
FIG. 5A: A scanning electron microscope (SEM) image of the $Au_xS_y^-$ structures formed at 1 h flow time before $NaBH_4$ reduction under the conditions as described in Example 1.
Figure 5B:
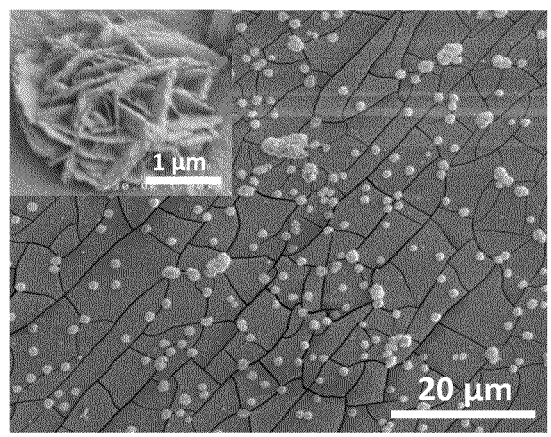
FIG. 5B: A scanning electron microscope (SEM) image of the $Au_xS_y^-$ structures having petal-like morphology as formed at 5 h flow time before $NaBH_4$ reduction under the conditions as described in Example 1.
Figure 5C:
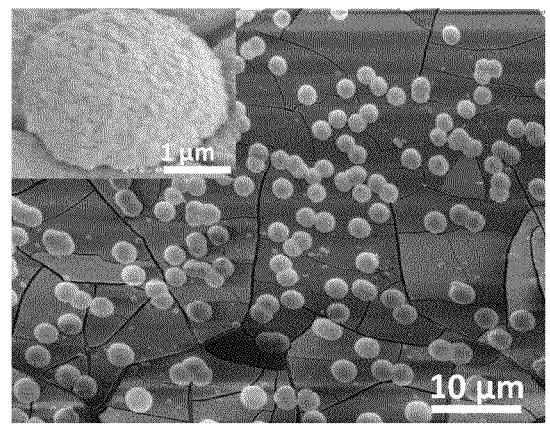
FIG. 5C: A scanning electron microscope (SEM) image of the $Au_xS_y^-$ structures formed at 9 h flow time before $NaBH_4$ reduction under the conditions as described in Example 1.

To efficiently carry out the techniques described herein, flow rates necessary to obtain metal catalyst coating having controlled morphology must be identified or determined. Examples of suitable flow rates are 1 ml/h to 100 ml/h and can be determined by size of the individual catalyst structures required, the dimension of the coating required, and other factors such as channel dimensions and reagent viscosities. Example 1 details the effects of flow rates and flow times on the size and morphology of gold nanostructures grown in a millifluidic device. FIGS. 5A, 5B, and 5C show the effect of flow time on nanostructure morphology and size after flow times of 1 h, 5 h, and 9 h, respectively, and relate to Example 1 below.

These metal salts may also be used in combination to obtain bi or tri-metallic catalyst coatings, which can be, for example, alloy or core-shell type structures.

Examples of catalytic reactions that can be catalyzed by these metal catalyst coating are outlines in Table 1 below.

TABLE 1

Examples of millifluidic device reactions.

| Catalyst | | Representative reactions | |
| --- | --- | --- | --- |
| Au nanostructured Millifluidic channel | Ethylene glycol to methyl glycolate [Tamas, M., 2012] Aqueous CO2 reduction [Yihong, C., 2012] | Propene to propene oxide [Jiahui, H., 2009] | Glucose and other carbohydrates to aldonic acids [Bright, T. K., 2013] [Yukihiko, M., 2006] |

TABLE 1-continued

Examples of millifluidic device reactions.

| Catalyst | | Representative reactions | |
|---|---|---|---|
| Pd nanostructured millifluidic channel | Levulinic acid hydrogenation [Pravin, P. U., 2011] | Oxidation of glycerol [Silvio, C., 2004] | Glycerol hydrogenolysis [Zhiwei, H., 2008] |
| Pt nanostructured millifluidic channel | Selective hydrogenation of carbonyl versus vinyl bonds [Erik, S., 2009] | Toluene Oxidation [Kim, S. C., 2011] | Oxidation of glycerol [Silvio, C., 2004] |
| Cu nanostructured millifluidic channel | hydroxylation of phenol by hydrogen peroxide [Edward, A. K., 2010] | Styrene oxidation [Hong-Kui, W., 2012] | Glycerol hydrogenolysis [Zhiwei, H., 2008] CO2 Reduction [Zhichuan, X., 2012] |
| Rh Nanostructured millifluidic channel | Hydrogenation of Arenes [Yuan, Y., 2012; Maya, B., 2008; Hubert, C., 2011] | Methoxy benzene to cyclohexanone [Hubert, C., 2009] | Chemoselective hydrogenation of phenylacetone [Fonseca, G. S. 2004] |

A list of complete references is given below:
1. Tamas, M.; Alfons, B., Potential of Gold Nanoparticles for Oxidation in Fine Chemical Synthesis, Annual Review of Chemical and Biomolecular Engineering, 2012, 3, 11-28.
2. Yihong, C.; Christina, W. L.; Matthew, W. K.; Aqueous CO2 Reduction at Very Low Overpotential on Oxide-Derived Au Nanoparticles, J. Am. Chem. Soc., 2012, 134 (49), 19969-19972.
3. Jiahui, H.; Tomoki, A.; Jérémy, F.; Tadahiro, F.; Takashi, T.; Masatake, H., Propene Epoxidation with Dioxygen Catalyzed by Gold Clusters, Angewandte Chemie International Edition, 2009, 48(42), 7862-7866.
4. Bright, T. K.; Dmitry, Y. M.; Catalytic oxidation of rare sugars over gold catalysts, Catal. Sci. Technol., 2013, 3, 297-307.
5. Yukihiko, M.; Yanachi, S.; and Yoshidae, T., Glucose Decomposition Kinetics in Water at 25 MPa in the Temperature Range of 448-673 K, Ind. Eng. Chem. Res., 2006, 45, 1875.
6. Pravin, P. U.; Jong-Min, L.; Dong, W. H.; Shiva, B. H.; Young, K. H.; Jong-San, C., Selective hydrogenation of levulinic acid to γ-valerolactone over carbon-supported noble metal catalysts, Journal of Industrial and Engineering Chemistry, 2011, 17(2), 287-292.
7. Silvio, C.; Paul, M.; Johnstonb, P.; Ken, G.; Christopher, J. K.; Gary, A. A.; Graham, J. H., Oxidation of glycerol using supported gold catalysts, Topics in Catalysis Vol. 27, Nos. 1-4, February 2004 (#2004).
8. Zhiwei, H.; Fang, C.; Haixiao, K.; Jing, C.; Xinzhi, Z.; Chungu, X., Highly Dispersed Silica-Supported Copper Nanoparticles Prepared by Precipitation—Gel Method: A Simple but Efficient and Stable Catalyst for Glycerol Hydrogenolysis, Chem. Mater., 2008, 20 (15), 5090-5099.
9. Erik, S.; Angelo, V.; Tamas, M.; Alfons, B.; Shape-Selective Enantioselective Hydrogenation on Pt Nanoparticles, J. Am. Chem. Soc., 2009, 131 (34), 12358-12367.
10. Kim, S. C.; Shim, W. G.; Lee, M. S.; Jung, S. C.; Park, Y. K., Preparation of platinum nanoparticle and its catalytic activity for toluene oxidation., J Nanosci Nanotechnol., 2011, 11(8), 7347-52.
11. Edward, A. K.; Anton, L. M.; Yulia, S. K.; Vitaliy, A. S.; Sergey, V. K.; Viktoriya, V. P.; Marta, Y. T.; Elena, L-L.; Jeffrey, A. S.; Scott, L. C.; Copper nanoparticles as active catalysts in hydroxylation of phenol by hydrogen peroxide, Applied Catalysis A: General, 2010, 385(1-2), 62-72.
12. Hong-Kui, W.; Chao-Yong, Y.; Li, T.; Wen-Juan, W.; Jian, F.; Ji-Hua, Z.; Wei-Guo, S.; Ag—Cu Bimetallic Nanoparticles Prepared by Microemulsion Method as Catalyst for Epoxidation of Styrene, Journal of Nanomaterials, Volume 2012 (2012), Article ID 453915, 8 pages.
13. Zhichuan, X.; Erica, L.; Yang, S-H.; Kimberly, H-S., Compositional dependence of the stability of AuCu alloy nanoparticles, Chem. Commun., 2012, 48, 5626-5628.
14. Fonseca, G. S.; Scholten, J. D.; Dupont, J. Iridium Nanoparticles Prepared in Ionic Liquids: An Efficient Catalytic System for the Hydrogenation, of Ketones, Synlett, 2004, 1525-1528.
15. Maya, B.; Audrey, D-N.; Alain, R.; Léon, G.; Patricia, B.; Antoine, G.; Franck, L.; A surfactant-assisted preparation of well dispersed rhodium nanoparticles within the mesopores of AlSBA-15: characterization and use in catalysis, Chem. Commun., 2008, 0, 2920-2922.
16. Yuan, Y.; Ning, Y.; Paul, J. D.; Advances in the Rational Design of Rhodium Nanoparticle Catalysts: Control via Manipulation of the Nanoparticle Core and Stabilizer, ACS Catal., 2012, 2 (6), pp 1057-1069.

The millifluidic device can be used to carry out any suitable reactions which employ chips with channels containing catalysts grown as described herein, including oxidation reactions as well as reduction reactions. The type of reaction carried out within a millifluid chip and reaction conditions such as temperature and pressure will dictate its materials of construction. For example, plastic chips are suitable for water-based reactions and reactions carried out at moderate temperatures, or up to about 600° F., depending on specific material heat tolerances. Suitable polymeric materials may include, for example, SU-8, polymethyl methacrylate (PMMA), polyetheretherketone (PEEK), polycarbonate (PC), and polydimethylsiloxane (PDMS), polyethylene, polytetrafluoroethylene, polyvinyl chloride, polyimide, TEFLON, polypropylene, Polystyrene (PS), and Cyclic Olefin Copolymer (COC), or combinations thereof. Physical heat tolerances of individual materials in addition to other factors such as corrosive resistance should be considered when selection material of construction. Where reaction conditions require higher operating temperatures or heated reagents, or generate high amounts of heat, such as organic reactions or high temperature as phase heterogeneous reactions, glass, silicon and stainless steel are more appropriate construction materials than heat-sensitive polymeric materials. Glass, silicon and steel may be normally used at most operating temperature, but higher material and fabrication costs minimize their use for operating temperatures under about 600° F. where more cost effective polymeric materials may be suitable. Glass, silicon, and steel are also preferred materials of construction where highly corrosive reagents, such as inorganic acids and chlorinated solvents, are used. Flow rates also governed by the nature of the material of construction by factors such as heat and corrosion tolerance. Millifluidic chips constructed from materials having lower heat tolerances can be coupled with heat exchange media to increase versatility. Heat exchange media may also be coupled to devices where it is necessary to maintain certain operating temperatures.

Determining the concentration of the reagents, flow rates, and time of flows are necessary for coating each type of metal catalyst. Two separate steps, as described above, may or may not be necessary depending on the type of the metal catalyst. In cases where surfactants or stabilizing agents such as meso-2, 3-dimercapto succinic acid (DMSA) act as a reducing agent to reduce gold, silver, copper salts to corresponding metals, two steps may not be required. Where reduction of metal salts require more powerful reducing agents such as NaBH4 or LiBH4, for example in the case of cobalt or iron salts, two separate steps may be needed.

Steps 1 and 3 can be combined into the first step, provided required control over morphology and dimensions of the coating can be maintained, in order to save time. For example, a metal salt and a surfactant, such as a gold salt and DMSA, may be introduced in one inlet channel and a reducing agent may be introduced in a second inlet channel to allow both solutions to react in a single step and deposit catalyst coatings within the millifludic channels.

The methods described herein can be used to coat metal and metal oxide catalysts, and combinations thereof, with dimensions and morphology onto the surface of a fluidic channel for a number of catalytically important reactions. The catalyst coating methods disclosed herein are applicable to other catalysts, as would be recognized by those of skill in the art. One example is where millifluidic channels are coated with gold catalyst having controlled dimensions and nano and micro structured morphology (see Example 1). This gold catalyst was utilized for catalysis of conversion of nitrophenol to aminophenol (see Example 2).

The catalyst coating methods described herein may be used to coat the channels of millifluidic chips. The coating method can also be used to coat various other types of flow channels (e.g., pipes, tubes etc.) for large scale production. For example, the coating process may be used to coat the SS tubes of microchannel heat exchangers such as those manufactured by Mezzo technologies in order to create large scale catalytic devices.

Regarding millifluidic chips, channels are typically either milled or hot embossed into a solid base plate, and then sealed with a cover plate. Tubing can also be inserted into the prepared channels, or be situated on a based plate in any desired orientation. Channel diameters range from about 0.01 to about 5.0 mm. Larger diameters can be preferable where the device operates at higher pressures, or where larger catalytic structures are desired. Operating pressures for millifluidic chips are typically in the range of about 1 to about 100 atm and maximum operating pressure is typically determined by the channel seals and construction material. Multi-material millifluidic chips may be constructed to increase pressure and temperature tolerances. For example, channels may be created in a polymeric plate, and tubular structures made of stainless steel or high temperature polymeric material can be placed and sealed within the channels. The same method can be employed to increase corrosion resistance and other properties of the channels without increasing cost or complexity of the base plate manufacturing process.

Examples of particular millifluidic chips are shown in FIG. 6A-F, which can contain a plurality of supply channels 610 which intersect at the beginning of a primary channel 611.

Primary channels may be up to about 10 mm in length, up to about 50 mm in length, up to about 100 mm in length, up to about 200 mm in length, up to about 500 mm in length, up to about 1,000 mm in length, or up to about 10,000 mm in length. In some embodiments primary channels may be between about 200 and about 250 mm in length, or specifically about 220 mm in length. Primary channel lengths may be even longer than about 10,000 mm in length where chip size permits or the prescribed chip use necessitates longer channels. When determining channel length, operating pressure, flow rates, residence times, reaction kinetics, and other parameters may be considered. Supply channels may be of various lengths which may depend upon available space on a chip, desired flow characteristics and other considerations. For example, supply lines leading to supply channels on a chip may create turbulent flow conditions, and supply channel length, width, or orientation may be adjusted to maintain turbulent flow, or to produce more laminar flow within the supply channels. The width of primary and supply channels may be up to about 0.01 mm, up to about 0.05 mm, up to about 0.10 mm, up to about 0.11 mm, up to about 0.12 mm, up to about 0.13 mm, up to about 0.14 mm, up to about 0.15 mm, up to about 0.25 mm, up to about 0.50 mm, up to about 0.75 mm, up to about 1.0 mm, up to about 1.25 mm, up to about 1.5 mm, up to about 1.75 mm, up to about 2.0 mm, up to about 2.5 mm, up to about 3.0 mm, up to about 4.0 mm, up to about 5.0 mm, up to about 6.0 mm, up to about 7.0 mm, up to about 8.0 mm, up to about 9.0 mm, up to about 10.0 mm, up to about 50.0 mm, up to about 100.0 mm, or up to larger widths depending on particular uses. Similarly, the width of primary and supply channels may be greater than about 0.01 mm, greater than about 0.05 mm, greater than about 0.10 mm, greater than about 0.11 mm, greater than about 0.12 mm, greater than about 0.13 mm, greater than about 0.14 mm, greater than about 0.15 mm, greater than about 0.25 mm, greater than about 0.50 mm, greater than about 0.75 mm, greater than about 1.0 mm, greater than about 1.25 mm, greater than about 1.5 mm, greater than about 1.75 mm, greater than about 2.0 mm, greater than about 2.5 mm, greater than about 3.0 mm, greater than about 4.0 mm, greater than about 5.0 mm, greater than about 6.0 mm, greater than about 7.0 mm, greater than about 8.0 mm, greater than about 9.0 mm, greater than about 10.0 mm, greater than about 50.0 mm, or greater than about 100.0 mm.

For example, channel diameters may be between about 0.01 mm and about 1.75 mm, between about 0.05 mm and about 1.5 mm, between about 0.10 mm and about 1.25 mm, between about 0.11 mm and about 1.0 mm, between about 0.12 mm and about 0.75 mm, between about 0.13 mm and about 0.50 mm, between about 0.14 mm and about 0.25 mm, or between about 0.15 mm and about 0.20 mm. Larger channel widths may be useful for operating at higher pressures and higher flow rates. For example, the millifluidic channels and methods relating thereto as described herein may be applied to scaled-up devices and processes such as industrial catalysis.

Millifluidic chips may be designed with a variety of channel configurations, including straight, serpentine, spiral, hydrodynamically focused basket weave geometry, Y-mixer, T-mixer, chamber geometry, zig zag channels, flow focusing, co-flowing, T-junction, and other orientations depending on the desired use.

For example, serpentine and spiral orientations allow for high channel lengths for a given millifluidic chip surface area. Generally, for laminar flow systems, a turn or bend in a channel will increase mixing at the fluid stream interface, which will result in an increasingly wide deposition strip for serpentine channels. The orientation of the supply channels 610 to the primary channel 611 will also have an effect on mixing and fluid velocity profiles within the channels. For example, chip 601 in FIG. 6A and chip 602 in FIG. 6B each may have supply and primary channels with diameters of 0.15 mm. At low flow rates, similar laminar flow is experienced after the supply channel streams combine, but turbulent flow and rapid mixing will be observed in chip 602 at flow rates greater than about 1.5-2 mL/min, due to the asymmetrical U orientation of the supply channels, while laminar flow rates will be maintained in chip 601. Flow of the combined supply streams can become turbulent at lower flow rates as the difference in the supply stream velocity vectors increase. Both flow direction and linear stream velocity can impact flow dynamics. Some embodiments relate to millifluidic chips which are capable of coating multiple primary channels simultaneously.

Figure 6A:
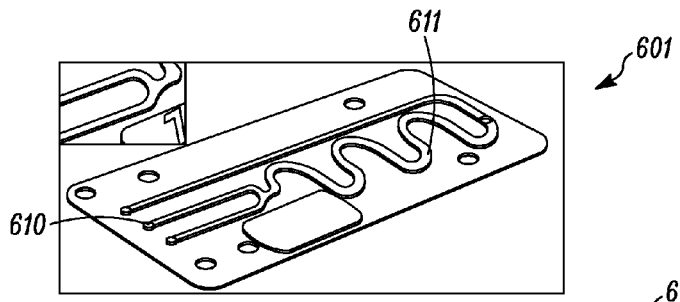
FIG. 6A: A perspective view of a "snake mixer" millifluidic chip purchased from Millifluidica, LLC (Baton Rouge, La.) and having two supply channels and a serpentine primary channel.
Figure 6B:
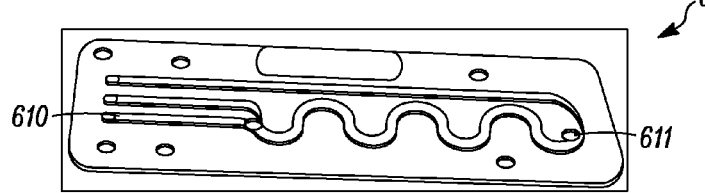
FIG. 6B: A perspective view of a "snake mixer" millifluidic chip purchased from Millifluidica, LLC (Baton Rouge, La.) and having two supply channels in an asymmetrical U-orientation to the serpentine primary channel.
Figure 6C:
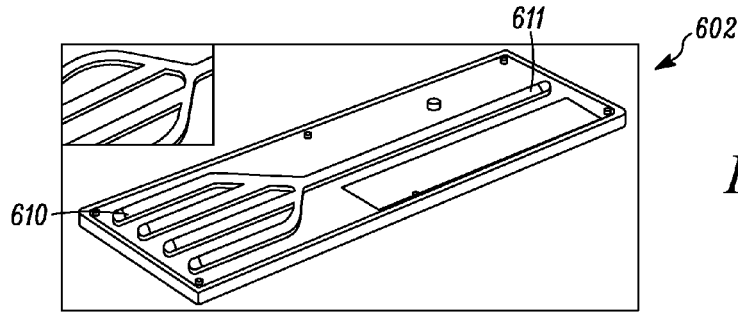
FIG. 6C: A perspective view of a hydrodynamically focused millifluidic chip purchased from Millifluidica, LLC (Baton Rouge, La.) and having four supply channels leading to a straight primary channel.
Figure 6D:
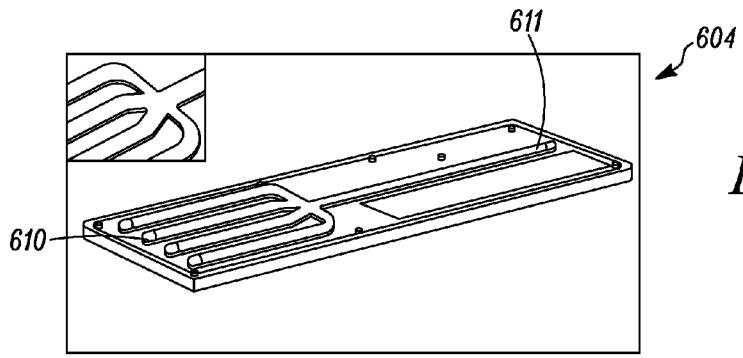
FIG. 6D: A top view of a hydrodynamically focused millifluidic chip purchased from Millifluidica, LLC (Baton Rouge, La.) and having two supply channels and a straight primary channel.
Figure 6E:
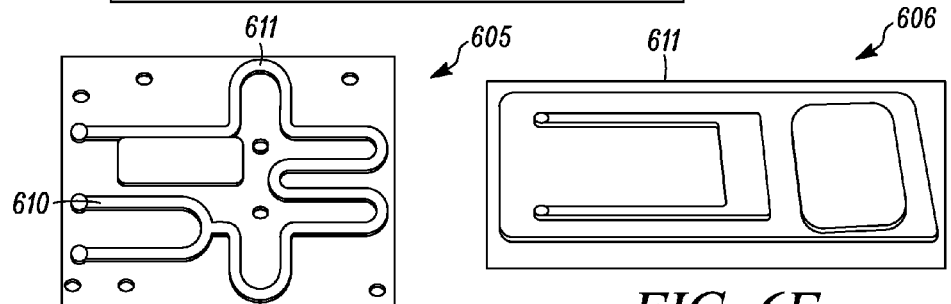
FIG. 6E: A top view of a "snake mixer" millifluidic chip purchased from Millifluidica, LLC (Baton Rouge, La.) and having two supply channels which empty into an irregular serpentine primary channel.
Figure 6F:
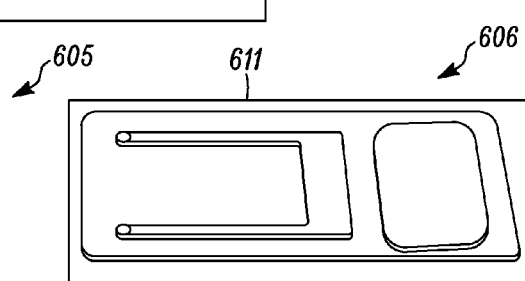
FIG. 6F: A top view of a millifluidic chip purchased from Millifluidica, LLC (Baton Rouge, La.) and having one supply channel leading to a chamber which empties into a primary channel.

Chips having chamber geometry, such as chip 606 in FIG. 6F, can be particularly useful for continuous flow cell culturing for analysis of biological fluids such as blood under microscope. Chambers incorporated into millifluidic chips may have a variety of widths depending on their use and the width of the millifluidic channels. For example, for a millifluidic chip having channel widths of about 0.15 mm may have chamber widths of greater than about 0.5 mm, greater than about 1 mm, greater than about 2 mm, greater than about 3 mm, greater than about 4 mm, or greater than about 5 mm. The channel cross sections may be circular, ovular, rectangular, or other various geometric shapes.

Hydrodynamically focused channels are able to encapsulate a center stream between two outer streams within the channels, which can be used to increase the width of the deposition strip, or to coat the channel with two or more different catalytic strips. For example, a stream of DMSA may be flown through a channel between two outer streams of a metal salt, or two outer streams of different metal salts. The same process may also be used for enzymes. An example of a hydrodynamically focused channel is shown in FIG. 9, having three input streams 910, 920 and 930, wherein the center input stream 920 is concentrated in the middle of the channel. FIGS. 6C and 6D also depict hydrodynamically focused channels. The orientation of channels in these chips affects flow dynamics. For example, chip 604 from FIG. 6D has a smaller node between the inlet channels, which provides hydrodynamic focus but also leads to different widths of the central channel or may also lead to droplet or slug formations.

It is within the primary channel that catalytic coating, reactions, diagnostic monitoring, continuous flow cell culturing, and other functions occur. In some embodiments, millifluidic chips will contain fluid diodes at channel intersections to prevent reagent backflow and contamination of supply channels. Characterization components and reactions controllers may be placed at spatial intervals throughout all of the channels. These components may be located on the chips or within the millifluidic device. Characterization components may include pressure gauges, flow meters, thermocouples, synchrotron X-ray sources, UV-VIS, fluoerescence, small angle X-ray, FT-IR, Raman spectroscopes, and other applicable components. Reaction controllers may include flow controllers, temperature controllers, heat exchange media, pH controllers, and other applicable components.

These millifluidic chips having catalyst-coated channels may be incorporated into hand-held devices and test kits which may be used for research, product and process development, and many other suitable uses which may include molecular reduction reactions, in situ material characterization, in situ reaction catalysis characterization, in situ reaction mechanism characterization, nanomaterial synthesis, nanostructured metal and metal oxide growth and coating of channels, bio-reactions, combinatorial chemistry, reactions involving homogeneous catalysts bound to channel walls, peptide synthesis, nucleic acid synthesis, synthesis of pharmaceutical intermediates, biofunctionalization of nanomaterials, and continuous flow cell culturing. Such chips may be suitable for any one of these various uses.

Droplet—based microfluidics have been applied to investigate polymerization reactions, and microbiology analysis and screening.[22] Millifluidic chips have been shown to be an ideal platform implementing milli-emulsions, micro-emulsions, and droplet-based fluidics for a variety of applications including single phase synthesis of ultrasmall nanoclusters and time resolved growth of nanoparticles. Droplet shapes may be substantially spherical or substantially cylindrical. Spherical droplets may range in diameter from micron size to millimeter size. Cylindrical droplets may have diameters ranging from micrometer to millimeter scale and lengths ranging from micrometer to centimeter scale.

Compact device sizes and portability further allow for diverse applications such as field analysis of air, water, soil, and other environmental samples, field analysis of microorganisms such as bacteria, various medical uses such as point of care synthesis of drugs, and other applications which require portability. These devices may remotely operate, using communication means such as Wi-Fi to transmit data for remote collection, storage, processing, and analysis. AC/DC power converters allow the device to be plugged into an AC power source or to run off of batteries. A given hand-held device may accept any number of chips which may be suitable for the above applications.

The millifluidic hand-held devices as shown in FIGS. 4A and 4B normally comprise a housing 421 with removable cover lid 423 which contains most device components, including any combination of a plurality of reagent reservoirs 421 or input ports, a plurality of pumps, one or more flow controllers such as 425, product and waste reservoirs, electronic circuit boards and other electronic components which may control the device, process data, or transfer data to an outside source via hard or wireless connections. Pumps and flow controllers will generally correspond to particular reagent reservoirs or input ports. The characterization components and reaction controllers discussed above may connect to external power, data collection units, computers, mobile devices, data storage units, and other pertinent sources. For example, heat exchange media may connect to water or other heat exchange fluid lines. Data may include any information relating to in situ probe outputs or operational values, such as concentration of components within a channel or device power usage, information relating to pump, flow controller, or other component operation, reagent reservoir levels, information relating to the contents of reagent reservoirs, information relating to operating conditions such as pressure, flow rate or temperature, or any other measurable quantities. Millifluidic chips 401 may be inserted into the millifludic device 420 for one or multiple uses. A manifold 410 may be used to secure reagent lines 411 and other elements to the chip, as shown. Flow rates within the components may be controlled with voltage, with programmable flow controllers, computers, or any mobile device such as cell phones.

Manifolds 410 may be part of the chip 401, may be a separate element which is removable from the chip, or may be a permanent element of the millifluidic hand-held device 420. A hand-held device may contain or be able to accept one or more chips 401, one or more manifolds 410, or a combination thereof. For example, a chip containing the flow channels coated with the catalyst can be connected to two external pumps and reservoirs small enough to fit into a compact box with external electrical connection to the pumps so that one has a hand held catalyst test kit.

The millifluidic hand-held device may contain a power source, which may be a battery or connection means such as 422 to an outside power source.

Figure 7:
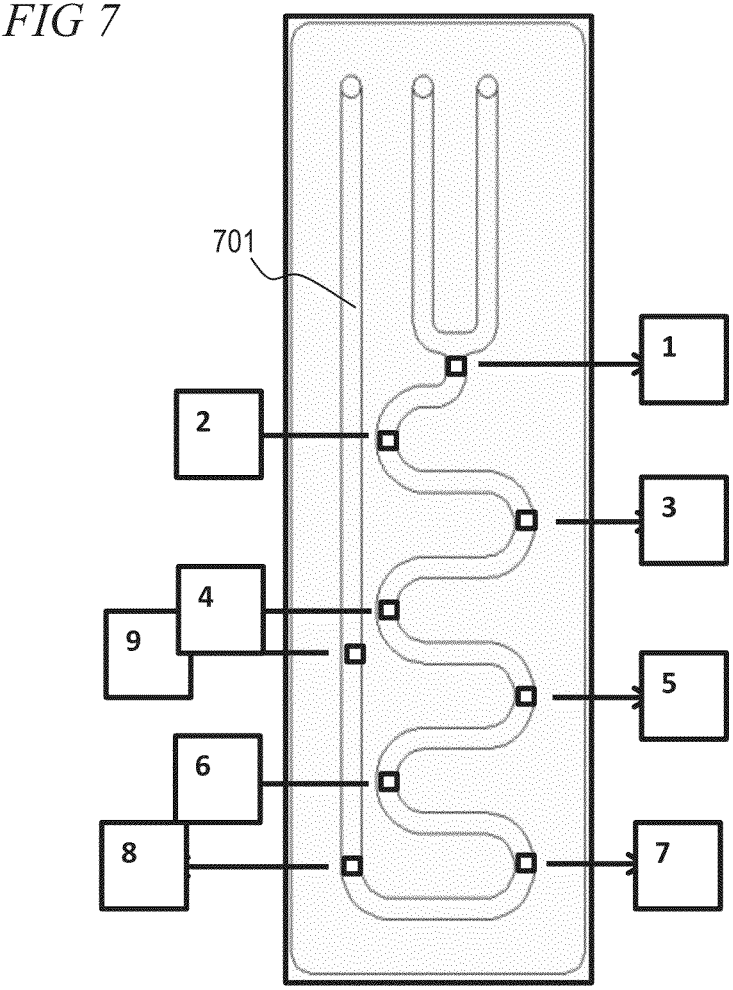
FIG. 7: A schematic view of a millifluidic chip, such as one which may be purchased from Millifluidica, LLC (Baton Rouge, La.), having two supply channels and a serpentine primary channel and indicating locations for multiple in situ time resolved probes.

The hand-held device may also contain one or more in situ time resolved probes, for example at points 1-9 throughout the millifluidic channel 701 shown in FIG. 7. In situ time-resolved probes may include synchrotron X-ray sources, UV-VIS, fluorescence, small angle X-ray, FT-IR, Raman spectroscopes, pressure sensors, thermocouples, particle size analyzers, or other suitable equipment.

The unique advantage of millifluidic chips and devices is that spatial resolution may be obtained at many points throughout the channels, and can be converted into time resolution at each point. Because the reaction mechanism will remain consistent at every spatial interval, regardless of reaction length and assuming negligible catalyst degradation where applicable, time resolutions at each spatial interval can be combined to create detailed models and understanding of reaction mechanisms, catalysis, and reaction chemistry, among other things. For example, products formed within the channels at a flow-rate of 10 mL/h can be analyzed with a time resolution of 5.4 ms. Millifluidic chips and related devices. These results, as shown below in Table 2 are a dramatic increase to traditional in situ probe methods such as "in a flask", where time resolution is about 100 micro seconds. Millifluidic chips and devices allow for nano-second resolution.

TABLE 2

Spatial and Time Resolution of a Millifluidic System at Various Flow Rates.

| | | Flow rate | | |
|---|---|---|---|---|
| Zone | Distance from the point of mixing (mm) | 1 ml/h Time Consumed | 10 ml/h Time Consumed | 60 ml/h Time Consumed |
| 1 | 0.05 | 54 mS | 5.4 mS | 0.9 mS |
| 2 | 15 | 16.20 S | 1.62 S | 0.27 S |
| 3 | 35 | 37.80 S | 3.78 S | 0.63 S |
| 4 | 55 | 59.40 S | 5.94 S | 0.99 S |
| 5 | 75 | 81.00 S | 8.10 S | 1.35 S |
| 6 | 95 | 102.60 S | 10.26 S | 1.71 S |
| 7 | 115 | 124.20 S | 12.42 S | 2.07 S |
| 8 | 135 | 145.80 S | 14.58 S | 2.43 S |
| 9 | 160 | 172.80 S | 17.28 S | 2.88 S |

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Catalyst Coating Method: Time Dependent Formation of Gold Nanostructures

Millifluidic chips (made of polyester terephthalate polymer) were purchased from Microplumbers Microsciences LLC. The chip had serpentine channels with dimensions of 2 mm (W)×0.15 mm (H)×220 mm (L) within which the experiments were performed. High precision, fully automated, pulsation free syringe pumps to flow the liquids within the chip were purchased from Cetoni Automation and Microsystems, GmbH. Fluidic connections between the reactor chip and the pump were made using FEP tubing (0.25 mm I.D., ¹⁄₁₆" O.D., Dolomite). The pumps were tested with water as solvent at different flow rates prior to the experiment to optimize the required flow rate. $HAuCl_4$ (Aldrich, 99.9%), meso-2,3-dimercaptosuccinic acid (DMSA, Aldrich, 98%), $NaBH_4$ (Aldrich, 98%), and Nanopure water (18.2 MΩ-cm) was used in all experiments (Examples 1 and 2).

A Standard solution of gold chloride (10 mM) was prepared by dissolving 118.2 mg of $HAuCl_4$ (Aldrich, 99.9%) in 30 mL of Nanopure water. A standard solution (20 mM) of dimercaptosuccinic acid (DMSA, Aldrich, 98%) was prepared my dissolving 109.2 mg of DMSA in 30 mL of Nanopure water. A standard solution (10 mM) of sodium borohydride ($NaBH_4$, Aldrich, 98%) was prepared by dissolving 11.34 mg of $NaBH_4$ in 30 mL of Nanopure water.

10 ml each of $HAuCl_4$ and DMSA solutions were taken into two separate syringes and were flown within the chip with a uniform flow-rate of 1 ml/h for a fixed amount of time (i.e. 1 h, 5 h, and 9 h). The as-formed $Au_xS_y^-$ structures within the chip were later reduced by flowing 10 mmol $NaBH_4$ within the chip for 15 min at 5 ml/h flow rate. The chip was finally washed with Nanopure water for 30 min at the same flow-rate before conducting the catalysis experiments.

Figure 8:
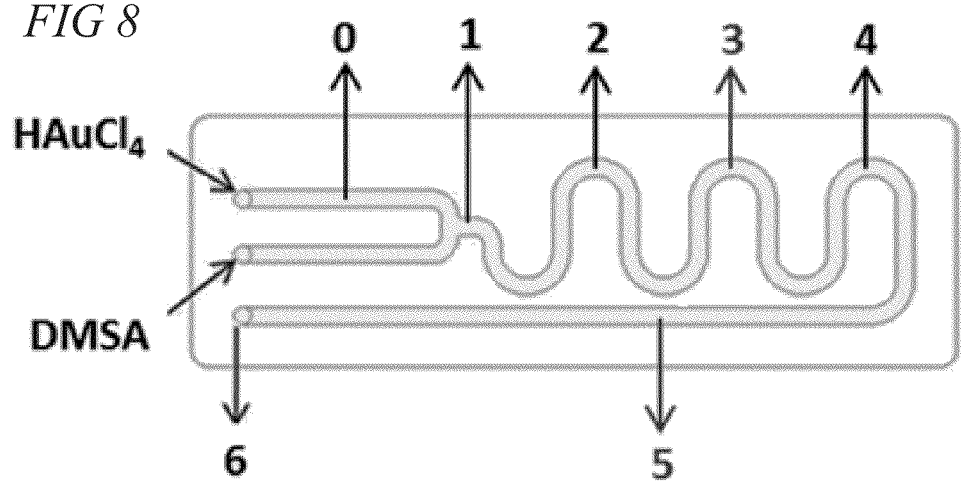
FIG. 8: A schematic view of a millifluidic chip, such as one which may be purchased from Millifluidica, LLC (Baton Rouge, La.), having two supply channels and a serpentine primary channel and indicating locations for multiple in situ time resolved probes as used in Example 1.

Step 1: 10 mL of the $HAuCl_4$ and DMSA solutions were taken into two separate syringes each and were connected to the chip's manifold as shown in FIG. 8

The millifluidic chip's serpentine channels had a length of 220 mm from point [1] to point [6] as shown in FIG. 8. The chip was purchased from Millifluidica, LLC at www.millifluidica.com.

The solutions were pumped into the channels with a uniform flow-rate of 1 mL/h for varying time intervals (i.e., 1, 3, 5, 7 and 9 h), with low Reynolds numbers of 2.57×10, resulting in the formation of $Au_xS_y^-$ nano-structures.

Step 2: The channels were washed with deionized nanopure water.

Step 3: A reducing solution of sodium borohydride ($NaBH_4$) was pumped for 15 min at 5 mL/h flow-rate.

Step 4: The chip was finally washed with Nanopure water for 30 min at the same flowrate.

The formation of $Au_xS_y^-$ structures and subsequent reduction to gold nanostructures is illustrated by Scheme 1.

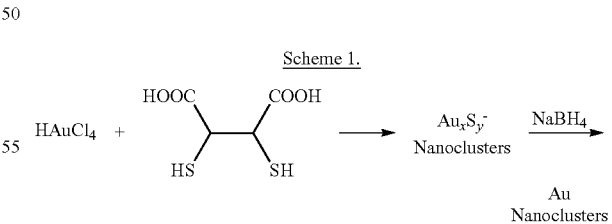

Scheme 1.

During Step 1, growth was monitored for 9 h with a constant flow-rate of 1 ml/h. The morphologies of the resultant gold structures formed at 1 h, 5 h, and 9 h were probed using scanning electron microscope (SEM), as shown in FIGS. 2A, 2C, and 2E, respectively. At 1 h, FIG. 5A, randomly-shaped polygonal nanoparticles of ~300 nm were observed. At 4 h the gold structures formed flower-like morphology ~2.4 μm in diameter with corrugated petal-like nanostructured features.

Figure 5D:
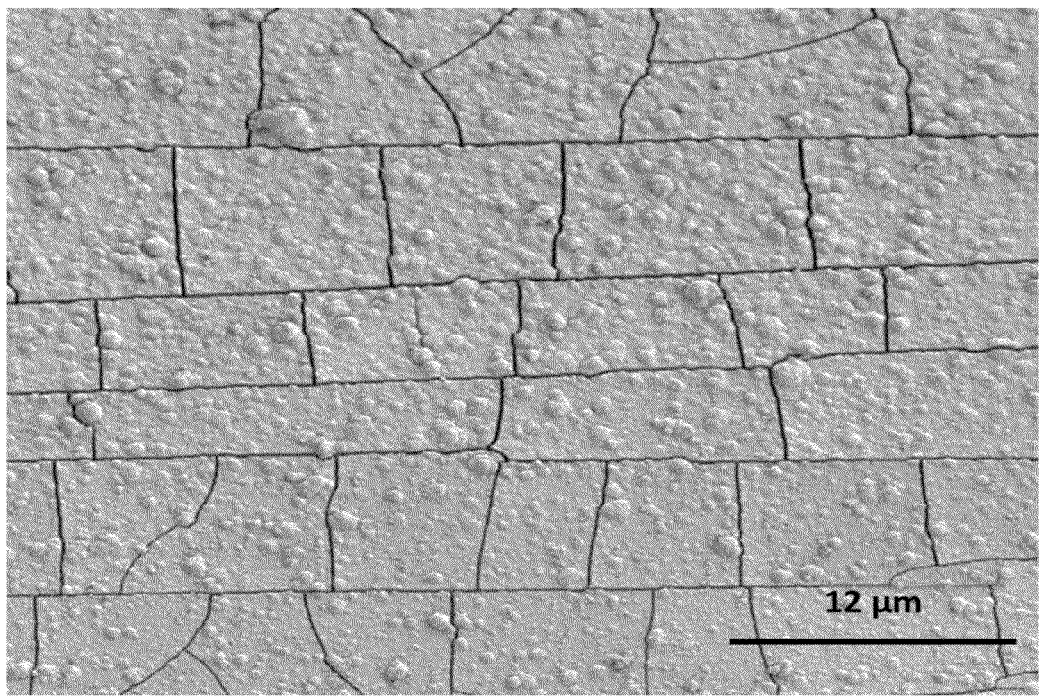
FIG. 5D: A scanning electron microscope (SEM) image of the $Au_xS_y^-$ structures formed at 9 h flow time before $NaBH_4$ reduction under the conditions as described in Example 1.

At 5 h, FIG. CB, the flower-like morphology was maintained, and diameter increased to ~3 μm. The multiple grooves between the petal-like structures ranged from 100-200 nm. At 7 h, flower-liked morphology was maintained. At 9 h, FIG. 5C, the flower-like morphology transformed into micro-hemispherical structures ~3 μm in diameter with rough, nano-structured, highly-porous surfaces, as shown also in FIG. 5D. The low 1 mL/h flow rates under the given conditions resulted in an extremely low Reynolds number of $2.57 \times 10^{-4}$, and flow was completely laminar. The two precursor solutions did not mix and flowed as separate solution streams on either side of the rectangular cross-section of the channel. As a result, the reaction occurred only at the interface of the two streams, producing first a controlled deposit of solid gold sulfide at the bottom center of the channel. After 9 h of flow, a thin yellow colored deposit strip ~100 μm in width consisting primarily of $Au_xS_y^-$ nanoclusters. The thickness and width of the deposit strip increased with time, although thickness did not exceed 27.5 μm.

Figure 5E:
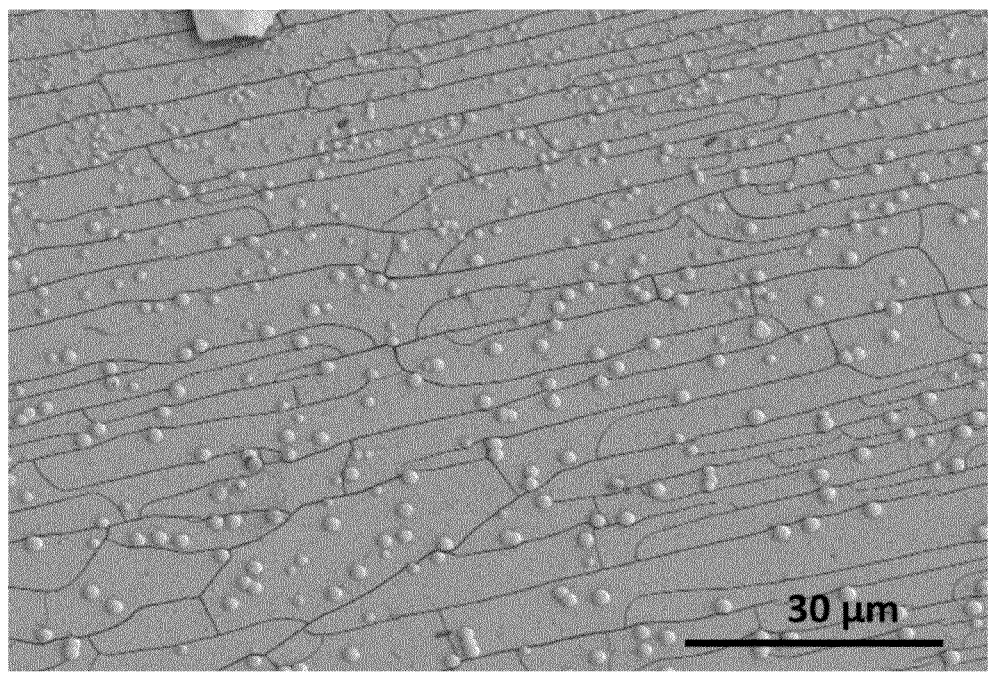
FIG. 5E: A scanning electron microscope (SEM) image of the $Au_xS_y^-$ structures formed after 45 min flow time before $NaBH_4$ reduction under the conditions as described in Example 1 but with an increased flow rate.

Flow rate was increased to 12 ml/h, and formation of an increased number of smaller spherical structures was noticed just after 45 minutes, as shown in FIG. 5E.

These results indicate morphology of coated nano-structures is at least dependent upon both flow times and flow-rate.

Example 2

Catalytic Reaction in a Catalyst Coated Flow Channel 15 mL of $9 \times 10^{-2}$ mM solution of 4-nitrophenol was mixed with 3.3 mL of 0.65 M $NaBH_4$ solution to form phenolate ions. This resultant solution was passed through the prepared gold catalyst coated within the flow channels (as described in Example 1) and the product was collected, to complete the reduction of 4-nitrophenol to 4-aminophenol catalyzed by gold, as illustrated in Scheme 2.

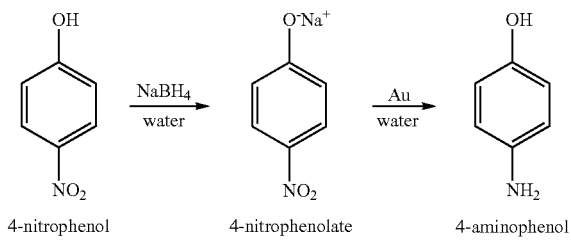

Scheme 2. Reduction Reaction of 4-NP to 4-AP.

Two catalysis reactions, (1) 4-nitrophenol reduction to 4-aminophenol and (2) hexacyanoferrate (III) reduction to hexacyanoferrate (II) were performed with three sets of gold catalysts (i.e. structures formed at 1 h, 5 h and 9 h respectively). In a typical reaction, 15 ml of $9 \times 10^{-5}$ mol solution of 4-nitrophenol was mixed with 3.3 ml of 0.65 mol $NaBH_4$ solution to form 4-nitrophenolate ion according to reported literature procedure.[31] The resultant solution was passed through the gold structures deposited chip at 5 ml/h flow rate (other flow-rates, viz. 20, 40 and 60 ml/h were also used) and the products collected were analyzed using UV-Vis spectrophotometer. Similarly, for the other catalysis reaction, 5 ml of $8.33 \times 10^{-4}$ mol Hexacyanoferrate (III) was mixed with 1 ml of $1 \times 10^{-2}$ mol $NaBH_4$ solution and the resultant solution was passed through the chips with same flow-rates.

Initially, 4-NP was mixed with $NaBH_4$ to form its more reactive 4-nitrophenolate ion (4-NPI) form, which was later introduced into the chip at a flow rate of 5 ml/h. It was converted into 4-AP catalyzed by the deposited gold nanostructures. In the absence of the gold catalyst, conversion of 4-NPI was 20%, whereas in the presence of gold catalyst (formed at 9 h deposition time), there was 90.5% conversion of the 4-NPI (FIG. 5b). The gold catalyst was also found to be catalytically active even after 80 hours of continuous flow reaction. In order to understand the influence of flow rate on catalysis, we carried out the catalysis at four different flow rates (5, 20, 40 and 60 ml/h) and monitored the conversion of phenolate ion at these flow rates. The highest conversion was found to take place at the lowest flow rate of 5 ml/h. This is not surprising as one can expect better contact with the catalyst at low flow rate where the residence time is higher. We have also demonstrated that the gold catalysts were active for conversion of ferricyanide to ferrocyanide. Here again, the gold catalyst (formed at 9 h flow time) had shown 85.5% conversion of the ferricyanide compared to 12% with no catalyst (Table 2).

The collected products were analyzed using UV-Vis spectra (using Shimadzu UV 3600 spectrophotometer) within the wavelength range of 250 nm to 500 nm to confirm the conversion of 4-NP. The catalytic activity of the reaction was estimated by obtaining the calibration curve of 4-NPI. The calibration curve can be acquired by plotting the experimentally observed absorption intensity (I) of 4-NPI at different standard concentrations. The peak heights (at 399 nm) for the UV-Vis absorption curves represent the absorption intensity (I) values and according to the Beer Lambert's law, any change in the peak height value would show corresponding change in its concentration. Therefore, the catalytic activity was estimated by finding the difference in initial and final concentrations of the reactant from the calibration curve.

For the catalysis experiment, conversion of 4-NP to 4-AP was monitored based on the UV-Vis analysis of the products obtained in comparison with the spectra of the standards. On mixing with $NaBH_4$ the absorption spectrum of 4-NP ($\lambda_{max}$ of 316 nm) was shifted to 399 nm indicating the formation of 4-NPI which on further reaction was converted to 4-AP ($\lambda_{max}$ of 301 nm) by flowing it through the millifluidic channels containing the gold nanostructures deposited at the center of the channels. A conversion rate of 90.5% was observed for 4-NP to 4-AP within the gold-deposited chip whereas the conversion was only 20% in a chip devoid of any gold catalyst. Most importantly, the gold catalyst was found to be catalytically active even after 80 hours of reaction. The results show the significance of millifluidics for continuous flow catalysis.

Example 3

Synthesis of Ultrasmall Copper Nanoclusters (UCNCs) in a Millifluidic Reactor

Chemicals used in this experiment include: Copper(II) nitrate hydrate (99.999%), sodium borohydride (≥98.0%), Sodium hydroxide pellets (99.998%) and O-[2-(3-Mercaptopropionylamino)ethyl]-O'-methylpolyethylene glycol ($M_w$ 5000) [MPEG], fumed silica, styrene (≥99.0%), tert-Butyl hydroperoxide solution—packed in PTFE bottles, ~5.5 M in decane (over molecular sieve 4 Å), anhydrous acetonitrile, methanol were obtained from Sigma-Aldrich. All chemicals were used as received without further purification. Water was supplied by a Barnstead Water Purifier Nanopure water system (18.3 MΩ cm).

The calculated Reynold's number shows the value of 10.74 even at the highest possible flow rate of 51.4 ml/h indicating that the fluids are operating at laminar regimes in spite of having a snake mixer. The Dean number was also as low as 1.65 even at the highest flow rate indicating that the curvature effect of the channel may be neglected. The mixing of the two inputs is dominated by convection as shown by the range of Peclet numbers from 178-1345 as shown in Table 3:

TABLE 3

Flow Characteristics Under Various Pressure and Flow Rates.

| Pressure (mbar) | Total flow rate (mL/h) | Total Velocity (m/s) | Re | De | Pe | Mean Residence time (s) | Variance (s^2) | Spread of Residence time (s) |
|---|---|---|---|---|---|---|---|---|
| 50  | 6.8  | 0.0076 | 1.42  | 0.22 | 178    | 47.49 | 852.29 | 93   |
| 100 | 14.3 | 0.0159 | 2.99  | 0.46 | 374.1  | 24.44 | 306.92 | 54.5 |
| 200 | 32.7 | 0.0363 | 6.82  | 1.05 | 854.4  | 16.56 | 181.84 | 44   |
| 300 | 51.4 | 0.0572 | 10.74 | 1.65 | 1344.8 | 9.02  | 92.13  | 27.5 |

Re: Reynold's number; De: Dean number; Pe: Peclet number

A millifluidic chip (made of polyester terephthalate polymer) was purchased from Microplumbers Microsciences LLC, which has serpentine channels with dimensions of 2 mm (W)×0.15 mm (H)×220 mm (L). Use FEP Tubing (purchased from Dolomite Centre) with dimensions of 0.25 mm I.D., 1/16" O.D., for connecting the chip to the pump. Use two different pumps for the two different experiments. P-Pumps (Mitos P-pump, Dolomite) were used for the first experiment (copper nanoparticles) and the millilfluidic device (Milliflu-dica) for the second experiment (gold nanoparticles). To minimize the problem of gas bubbles within the channels, freshly prepared $NaBH_4$ solution was left open to stand for ~10-15 min before pumping into the chip so that the gas bubbles escape from the solution.

A first solution was prepared by dissolving 174 mg (0.95 mmol) of copper(II) nitrate and 610 mg (0.122 mmol) of O-[2-(3-mercaptopropionylamino)ethyl]-O'-methylpolyethylene glycol in 28 mL of nanopure water. A second solution was prepared by combining 111 mg (2.93 mmol) of sodium borohydride and 102 mg (2.78 mmol) sodium hydroxide in 28 mL (pH~13) in a different vial and connect it with the other input channel.

Both solutions were simultaneously injected into the millifluidic reactor at different flow-rates (given below) and collect the resulting UCNCs at the outlet in glass vial, which was purged with nitrogen and stored under nitrogen. The pumps were operated under different constant pressures of 50 mbar (6.81 mL/h), 100 mbar (14.31 mL/h), 200 mbar (32.7 mL/h) and 300 mbar (51.4 mL/h) at room temperature for the synthesis of UCNCs at different flow-rates.

Well dispersed and uniform sized copper nanoclusters with a narrow size distribution were obtained using the millifluidic chip set-up. The different flow-rates used for synthesis did not have a significant effect on the size of the clusters. Nevertheless, with increase in the flow-rate, there is an observable improvement in the narrowing of the size distribution. UCNCs with a best narrow size distribution were obtained at a flow-rate of 32.7 mL/h. The size of UCNCs formed at 32.7 mL/h flow-rate has an average diameter of 1.2 nm (FIG. 1b).

In typical microfluidic systems, with channel sizes in the range of 10-100 μm, possible flow rates are only in the range of 0.03 to 4 ml/h.[26] The millifluidic system, on the other hand, offered the possibility to reach flow rates as high as 51.4 ml/h.

It appears that the reaction is confined mostly at the interfacial zone between the two streams within the millifluidic reactor channel.

It is also important to note that the gas bubble formation typical for $NaBH_4$ reductions is minimized to large extent at high flow rates that we used in the synthesis. Also, by leaving the as prepared $NaBH_4$ solution for some time (10-15 min) and cooled we were able to ensure that the bubble formation is minimal. Combination of high flow rates and ensuring proper preparation of reducing agent solution, one can minimize the gas formation and therefore, one can make a strong case for single phase laminar flow with a smooth parabolic velocity profile and a well-defined residence time.

At high flow rates of 32.7 ml/h (200 mbar) and 51.4 ml/h (300 mbar) the mean residence times were found to be extremely small (approximately 5~10 s) indicating that under these flow conditions there is an opportunity to separate the nucleation and growth stages, if kinetics of the reaction permits, with a potential opportunity to obtain UNCs with narrower size distribution (see supporting info). Also, one would expect narrower size distribution of particles as the spreads of residence time tend to narrow at these high flow rates. The high velocity flow characteristics as shown through numerical simulations also demonstrate similarities between microfluidic and millifluidic systems [22, 24, 28] However, it is easier to attain higher flow rates in a millifluidic reactor due to smaller pressure drops compared to microfluidic reactors; which are difficult to fabricate to sustain high pressures.

Example 4

Continuous Flow Copper Catalysis—Oxidation of Styrene

The oxidation of olefins in general and oxidation of styrene in particular is of great interest and importance in the production of fine chemicals and chemical intermediates. The UNCs synthesized at a flow rate of 32.7 ml/h from Example 3 were tested using oxidation of styrene as a model reaction, as shown in Scheme 3.

Scheme 3. Oxidation of styrene using copper nano-cluster catalyst.

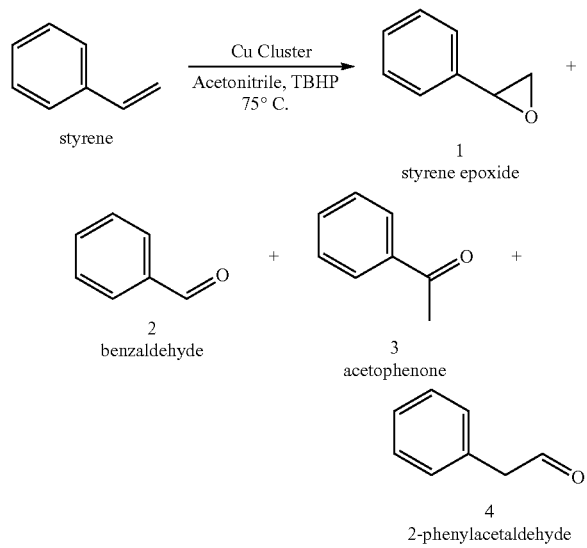

[a]. 1.6 mmol of styrene, 20 ml of acetonitrile, 125 mg of supported catalyst, time for 16 h, temperature of oil bath at 75° C.; t-butyl hydroperoxide (TBHP, 5 mol %) is added. (b). 1: styrene epoxide; 2: benzaldehyde; 3: acetophenone; 4: 2-phenylacetaldehyde In our investigations with silica supported UCNCs, the styrene oxidation resulted in several reaction products (Scheme 3) with a high (67%) selectivity for benzaldehyde as the major product and with ~72% overall conversion of the styrene, as shown in Table 4.

TABLE 4

Styrene oxidation catalyzed by supported UCNCs

| Entry | Cu cluster loading (%) | Styrene conversion (mol %) | Product selectivity (mol %) | | | |
|---|---|---|---|---|---|---|
| | | | 1 | 2 | 3 | 4 |
| $Cu_n$—$SiO_2$ | 5 | 72 | 28 | 67 | 4 | 1 |

The oxidation reaction without catalyst occurs very slowly with a final conversion of only 7%.

Ultra-small gold nanoclusters have been recently investigated for their size dependent catalytic activity for styrene oxidation. For example, silica supported $Au_{25}$, $Au_{38}$, $Au_{144}$ clusters exhibited catalytic conversion of styrene with conversions more than 90% (reactivity $Au_{144}$>$Au_{38}$>$Au_{25}$) with highest selectivity for benzaldehyde (~100%).

Example 5

Synthesis of Copper Nanoparticles Using the Slugs Generated within the Millifluidic Reactor The performance of the millifluidic reactor was tested by synthesizing copper nanoparticles at different flow ratios in squeezing regime: a lower flow ratio ($Q_c$:$Q_d$=1:1, slug length=7.13 mm) and a higher flow ratio ($Q_c$:$Q_d$=4:1, slug length=4.35 mm). Each slug formed within the millifluidic reactor by the two immiscible fluidic flows (tetradecane and water) acted as a mini-reactor for reagent combination and reaction. Tetradecane was used as a non-solvent carrier fluid injected through two outer inlet channels of the millifluidic reactor. The two aqueous based reagent streams were delivered through the two center inlet channels under nitrogen at room temperature. One of the centered inlets contained solution of copper nitrate and polymeric surfactant, O-[2-(3-Mercaptopropionylamino)ethyl]-O'-methylpolyethylene glycol (Mw 5000) [MPEG], while the other contained the solution of sodium borohydride and sodium hydroxide in water. We have previously demonstrated the utility of MPEG in a single phase millifluidic synthesis to provide stable metal cluster colloids due to better coordination with metals, steric stabilization and superior colloidal stability.[24b] In the current situation where copper nanoparticle formation took place within a slug, the surfactant was able to provide similar advantages due to better chelation with copper surface through bi-dentate ligands present at the terminal. Copper nanoparticle formation took place as each individual fused slug traversed the long switchback channel. The copper nanoparticles formed were collected under inert atmospheric conditions (nitrogen flow) at two different flow rates. As seen from the Transmission Electron Microscopy (TEM) images in FIG. 6, lower flow ratio led to the formation of bigger (14.09 nm σ=3.41) but less uniform particles compared to those (5.99 nm σ=1.14) formed at a higher flow rate. In comparison with copper nanoparticles formed within the slug versus a single phase in a millifluidic reactor one could delineate some distinct differences on the characteristics of the copper nanoparticles formed. Both the snake mixer type millifluidic device previously used for single phase synthesis[24b] as well as the current segmented flow focused millifluidic devices provided size controlled copper nanoparticles while retaining the spherical shape of the particles. At lower flow rate in the segmented flow millifluidic device yielded much bigger sized nanoparticle (14.09 nm σ=3.41) while the single phase flow synthesis at a comparable flow rate of 6.8 ml/h flow rate resulted in obtaining copper nanoparticles of average diameter 3 nm with broader size distribution.[23b] At a higher flow rate (850 µL/min~51 ml/h) both types of millifiluidic devices yielded very small copper nanoparticles of comparable size (2-3 nm).

The results indicate that the shorter slugs yield more uniform nanoparticles. This is likely to be due to better mixing and reduced axial dispersion inside the shorter slugs. Tice et al., have studied the mixing performances of aqueous slugs inside a T-junction microfluidic device, and they concluded that the shorter slugs have better mixing due the relatively small amount of fluid. However, in our case where millifluidic channels have been used, the larger dimensions resulted in longer slugs. This could be one of the reasons for the inability to produce uniform nanoparticles under the selected flow conditions. Therefore, both geometry as well as flow conditions need to be further optimized in order to arrive at optimum millifluidic design necessary to produce more uniform nanoparticles.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A hand-held millifluidic device comprising:
two or more reagent reservoirs, and
a removable chip having
two or more millifluidic supply channels, each of the two or more millifluidic supply channels being capable of fluidly communicating with one of the two or more reservoirs,
a primary channel in fluid communication with the two or more millifluidic supply channels, the primary channel having a width of about 0.15 millimeters to about 10 millimeters and a strip of catalytic structures along at least a portion of the primary channel having a width less than the width of the primary channel, wherein the strip of catalytic structures is formed by flowing a reagent solution and a reducing agent solution through the supply channels into the primary channel at laminar flow conditions such that a distinct reagent stream and a distinct reducing agent stream are achieved within the primary channel forming a stream interface whereat catalytic structures are formed on the primary channel having controlled dimensions and morphology.

2. The device of claim 1 wherein the catalytic structures have diameters of 0.01 microns to about 5,000 microns.

3. The device of claim 1 further comprising one or more in situ time resolved probes.

4. The device of claim 1 wherein the primary channel is between about 0.01 millimeters and about 5.0 millimeters in width.

5. The device of claim 1 wherein the primary channel configuration is straight, serpentine, irregular serpentine, zig zag, spiral, chambered, or a combination thereof.

6. The device of claim 1 wherein the orientation of the supply channels to the primary channel is that of a hydrodynamically focused basket weave geometry, symmetrical U-orientation, asymmetrical U-orientation, or T-orientation.

7. The device of claim 1 wherein the channels comprise microscale or milliscale tubing made of glass, stainless steel, silicon, polymeric materials, or a combination thereof, and the tubing is laid into a chip base-plate.

8. The device of claim 1 further comprising a plurality of chips capable of carrying out one or more reactions or processes simultaneously.

9. The device of claim 1, wherein the device is capable of performing one or more of a molecular reduction reaction, an in situ material characterization, an in situ reaction catalysis characterization, an in situ reaction mechanism characterization, a nanomaterial synthesis, a nanostructured metal growth, a nanostructured metal oxide growth, a continuous flow cell culture, an enzymatic catalytic reaction, a bio-molecular catalytic reaction, combinatorial chemistry, reactions involving homogeneous catalysts bound to the channel walls, peptide synthesis, nucleic acid synthesis, synthesis of pharmaceutical intermediates, and biofunctionalization of nanomaterials.

10. The device of claim 1, wherein the catalytic structures are positioned in a plurality of strip formations in the primary channel.

11. The device of claim 1, wherein the morphology of the catalytic structures is one or more of hemispherical, and flower-like or petaled, with a size of 0.01 microns to about 5,000 microns.

12. The device of claim 1, wherein the morphology of the catalytic structures is porous and the pores have a mean diameter of about 1 nanometer to about 500 nanometers.

13. The device of claim 1, wherein the catalytic structures comprise one or more of platinum, palladium, copper, silver, iron, rhodium, and cobalt.

14. The device of claim 2, wherein catalytic structures have morphological features in the range of 1 nm to about 500 nm.

15. The device of claim 1, wherein the catalytic structures are one or more of mono-metallic, bi-metallic, and tri-metallic.

16. The device of claim 10, wherein the catalytic structures comprise a first catalytic strip and a second catalytic strip, wherein one or more of the morphology, chemical composition, and thickness of the first catalytic strip differs from the second catalytic strip.

* * * * *